(12) United States Patent
Goldstein

(10) Patent No.: US 6,630,302 B1
(45) Date of Patent: Oct. 7, 2003

(54) METHODS AND COMPOSITIONS FOR DETERMINING SPECIES OF BACTERIA AND FUNGI

(75) Inventor: Richard N. Goldstein, Cambridge, MA (US)

(73) Assignee: The Trustees of Boston University, Boston, MA (US)

( * ) Notice: Subject to any disclaimer, the term of this patent is extended or adjusted under 35 U.S.C. 154(b) by 0 days.

(21) Appl. No.: 09/463,588

(22) PCT Filed: Jul. 24, 1998

(86) PCT No.: PCT/US98/15464

§ 371 (c)(1),
(2), (4) Date: Apr. 4, 2000

(87) PCT Pub. No.: WO99/05325

PCT Pub. Date: Feb. 4, 1999

Related U.S. Application Data

(60) Provisional application No. 60/053,097, filed on Jul. 25, 1997.

(51) Int. Cl.$^7$ .............................. C12Q 1/68; C12Q 1/70; C12Q 1/02; C12Q 1/04; C12Q 1/06; C12N 9/16; C12N 1/00

(52) U.S. Cl. .............................. 435/6; 435/5; 435/29; 435/34; 435/39; 435/804; 435/822; 435/196; 536/24.3; 536/24.32

(58) Field of Search .......................... 435/6, 5, 29, 34, 435/39, 4, 822, 804, 196; 935/78

(56) References Cited

U.S. PATENT DOCUMENTS

| | | | |
|---|---|---|---|
| 4,671,958 A | 6/1987 | Rodwell et al. | 424/85 |
| 4,717,653 A * | 1/1988 | Webster et al. | 435/5 |
| 4,831,122 A | 5/1989 | Buchsbaum et al. | 530/389 |
| 4,867,973 A | 9/1989 | Goers et al. | 424/85.91 |
| 4,957,738 A | 9/1990 | Patarroyo | 424/88 |
| 4,958,009 A | 9/1990 | Bjorn et al. | 530/389 |
| 4,980,457 A | 12/1990 | Jansen et al. | 530/391 |
| 5,208,021 A | 5/1993 | Johnson et al. | 424/85.91 |
| 5,332,567 A | 7/1994 | Goldenberg | 424/1.49 |
| 5,364,762 A | 11/1994 | Dornmair et al. | 435/7.24 |
| 5,487,982 A | 1/1996 | Salter | 435/69.1 |
| 5,495,423 A | 2/1996 | DeLisi et al. | 364/496 |
| 5,518,888 A | 5/1996 | Waldman | 435/7.23 |
| 5,578,706 A | 11/1996 | Ghetie et al. | 530/391.7 |
| 5,608,039 A | 3/1997 | Pastan et al. | 530/387.3 |
| 5,635,603 A | 6/1997 | Hansen et al. | 530/391.5 |
| 5,652,342 A | 7/1997 | Zimmerman et al. | 530/403 |
| 5,654,144 A * | 8/1997 | Mann et al. | 435/6 |
| 5,657,255 A | 8/1997 | Fink et al. | 364/578 |

FOREIGN PATENT DOCUMENTS

| WO | WO 97/01647 | * 1/1997 | |
|---|---|---|---|

OTHER PUBLICATIONS

Gravelle et al., "The Targeting of CD4+ T Lymphocytes to A B Cell Lymphoma. A Comparison of Anti–CD3–Anti–Idiotype Antibody Conjugates and Antigen–Anti–Idiotype Antibody Conjugates", J. Immunology, 142 4079–4084 (1989).

Ihle et al., "Antibody–targeted Superantigens Induce Lysis of Major Histocompatibility Complex Class II–negative T–cell Leukemia Lines", Cancer Research 55, 623–628 (1995).

Reiter et al., "Peptide–specific killing of antigen–presenting cells by a recombinant antibody–toxin fusion protein targeted to major histocompatibility complex/peptide class I complexes with T cell receptor–like specificity", Proc. Natl. Acad. Sci. USA 94, 4631–4636 (1997).

Holzer et al., "T–cell stimulation and cytokine release induced by staphylococcal enterotoxin A (SEA) and the SEAD227A mutant", Immunology, 90 74–80 (1997).

Carayanniotis et al., "Adjuvant–free IgC responses induced with antigen coupled to antibodies against class II MHC", Nature, 327 59–61 (1987).

Snider et al., "Targeted Antigen Presentation Using Crosslinked Antibody Hetroaggregates", J. Immunology, 139 1609–1616 (1987).

Berg et al., "Comparing macrophages and dendritic leukocytes as antigen–presenting cells for humoral responses in vivo by antigen targeting", Eur. J. Immunol., 24 1262–1268 (1994).

Snider et al., "Intranasal antigen targeting to MHC class II molecules primes local IgA and serum IgG antibody responses in mice", Immunol., 90 323–329 (1997).

Juliano, "Drug Delivery Systems. Characteristics and Biomedical Applications", Chapter 8, Oxford University Press, New York (1980).

Steinbach et al., "Transmissibility of Pseudomonas Cepacia Infection in Clinin Patients and Lung–Transplant Recipients with Cystic Fibrosis", N.E. J. of Med., 331 981–987 (1994).

Goldstein et al., "Structurally Variant Classes of Pilus Appendage Fibers Coexpressed from Burkholderia (Pseudomonas) cepacia", J. Bacteriology, 177 No. 4, 1039–1052 (1995).

(List continued on next page.)

Primary Examiner—Kenneth R. Horlick
Assistant Examiner—Cynthia Wilder
(74) Attorney, Agent, or Firm—Weingarten, Schurgin, Gagnebin & Lebovici LLP

(57) ABSTRACT

Methods and compositions are described for methods and compositions for determining the species for an unknown bacterium (or fungus) in a sample. The approach, which utilizes Ribosomal operon sequences, permits one to identify important bacteria (or fungi) pathogens in a clinical setting.

7 Claims, 6 Drawing Sheets

OTHER PUBLICATIONS

Sun et al., "The Emergence of a Highly Transmissible Lineage of cbl+ Pseudomonas (Burkholderia) cepacia causing CF centre Epidemics in North America and Britian", Nature Medicine, 1 No. 7, 661–666 (1995).

Arthur et al., "Restriction Fragment Length Polymorphisms Among Uropathogenic *Escherichia coli* Isolates: Pap–Related Sequences Compared with rrn Operons", Infection and Immunity, 58 No. 2, 471–479 (1990).

* cited by examiner

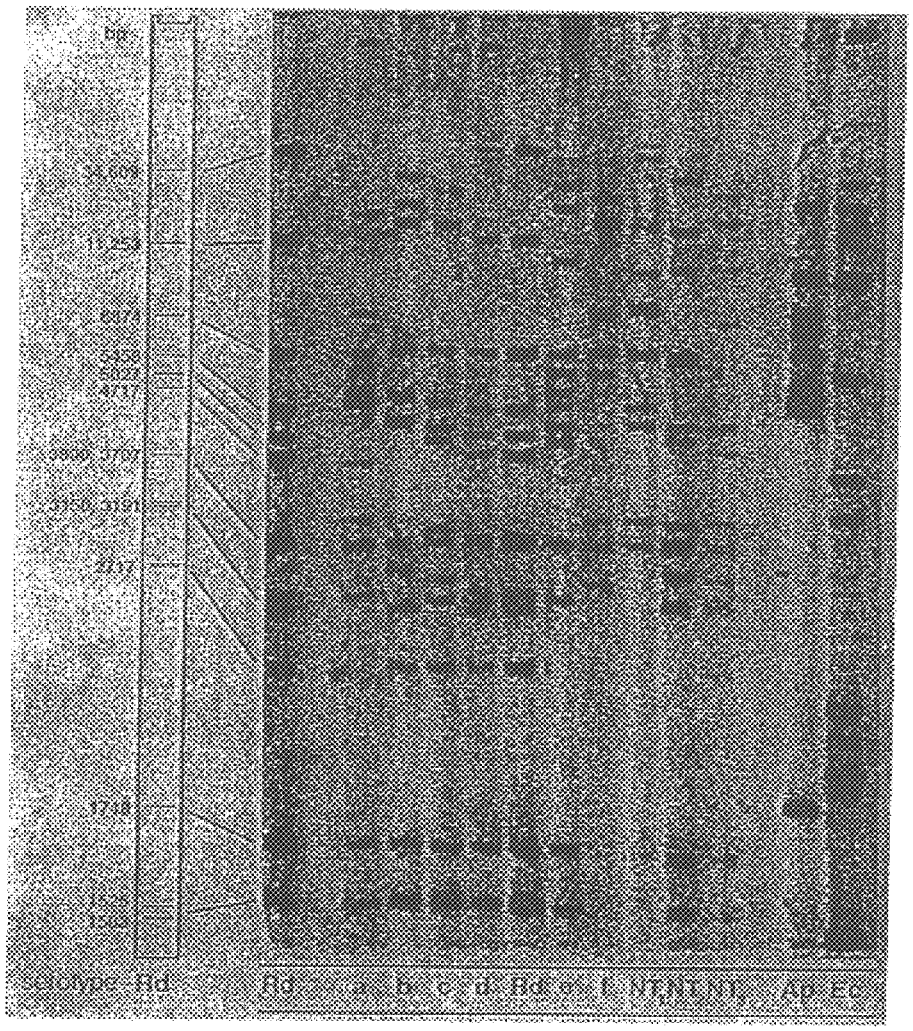

LEGEND.
Leftmost portion of the figure depicts the predictable EcoRI ribotype RFLP profile of the genomically sequenced H. influenzae strain Rd. Actual RFLP profiles of this strain appears in lanes 1 and 6 (so labeled). Other H. influenzae isolates, as indicated, are serotypes a, c, c, d, e, f and NT (non-typable, i.e. unencapsulated). EcoRI RFLPs of 2 non-H. influenzae isolates are shpwn at the farthestmost right lanes, that for A. pleuroneumonia (Ap) and E. coli (Ec).

*FIG. 2*

LEGEND.
Leftmost portion of the figure depicts the predictable EcoRI ribotype RFLP profile of the genomically sequenced E. coli strain MG1655. Actual RFLP profiles of this strain appear in lanes 1, 8 and 17.

METHODS AND COMPOSITIONS FOR DETERMINING SPECIES OF BACTERIA AND FUNGI

This application for patent under 35 U.S.C. 111(a) claims priority to Provisional Application Ser. No. 60/053,097 filed Jul. 25, 1997 under 35 U.S.C. 111(b).

This invention was made with Government Support under Grant Number DK-RO1-AI37728 awarded by the National Institute of Health. The government may have certain rights in the invention.

FIELD OF THE INVENTION

The present invention relates to the identification of species, and in particular, methods and compositions for distinguishing between bacterial and fungal species and determining the identity of bacterial and fungal pathogens in biological samples.

BACKGROUND

The detection and identification of microorganisms recovered from clinical specimens or environmental sources is an important aspect of clinical microbiology, as this information is important to physicians in making decisions related to methods of treatment. In order that a particular microorganism is identified correctly and consistently, regardless of the source or the laboratory identifying the organism, reproducible systems for identifying microorganisms are critical. As stated by Finegold, "The primary purpose of nomenclature of microorganisms is to permit us to know as exactly as possible what another clinician, microbiologist, epidemiologist, or author is referring to when describing an organism responsible for infection of an individual or outbreak" (S. Finegold, "Introduction to summary of current nomenclature, taxonomy, and classification of various microbial agents," *Clin. Infect. Dis.*, 16:597 [1993]).

Classification, nomenclature, and identification are three separate, but interrelated aspects of taxonomy. Classification is the arranging of organisms into taxonomic groups (i.e., taxa) on the basis of similarities or relationships. A multitude of prokaryotic organisms has been identified, with great diversity in their types, and many more organisms being characterized and classified on a regular basis.

Classification has been used to organize the seemingly chaotic array of individual bacteria into an orderly framework. Through use of a classification framework, a new isolate can be more easily be characterized by comparison with known organisms. The choice of criteria for placement into groups is currently somewhat arbitrary, although most classifications are based on phylogenetic relationships. An example of the arbitrariness of bacterial classification is reflected in the genetic definition of a "species" as being strains of bacteria that exhibit 70% DNA relatedness, with 5% or less divergence within related sequences (Baron et al., "Classification and identification of bacteria," in *Manual of Clinical Microbiology*, Murray et al. (eds.), ASM Press, Washington, D.C., pp. 249–264 [1995]).

Generally, identification of a bacterium is based on its overall morphological and biochemical patterns observed in culture. Indeed, this is the primary technique employed today in clinical laboratories. Of course, this approach is flawed by the fact that diverse organisms can have similar morphologies and/or biochemical requirements. Moreover, numerous organisms associated with disease may not be cultured in vitro. Indeed, some do not grow well in traditional in vivo culture systems, such as cell cultures or embryonated eggs, nor in vitro such as various nutrient agars and broths.

What is needed is a more defined system for speciation, and in particular, speciation of bacteria and fungi. Such an approach should be amenable to automation, permitting the approach to be used routinely in a clinical laboratory.

SUMMARY OF THE INVENTION

The present invention relates to the identification of microbial species, and in particular, methods and compositions for determining the species for an unknown bacterium (or fungus) in a sample. The methods and compositions of the present invention permit distinguishing between bacterial species (or between fungal species) and determining the identity of bacterial (or fungal) pathogens in biological samples. The present invention contemplates a method of speciation that does not require the sequencing of nucleic acid from biological samples. Instead, the method is based on detection of heretofore unknown uniquely conserved portions of ribosomal nucleic acid, such portions being conveniently revealed by restriction digestion of DNA encoding ribosomal nucleic acid, i.e. rRNA genes.

In one embodiment of the method of the present invention for speciation, the present invention contemplates analysis of one or more so-called Ribosomal operons ("rrn") of a clinical isolate, the operon comprising three genes often arranged in the order 16S-23S-5S for prokaryotes (and 18S-5.8S-25S for eukaryotes), with "spacer" DNA separating each gene (hereinafter represented by: 5'-16S -spacer-23S-spacer-5S-3'). The present invention contemplates that the analysis of at least one of these operons in an unknown bacterial or fungal species (when evaluated for the "signature band sets" of a particular species, the signature bands and methods for determining signature bands herein described) allows for accurate speciation.

It is not intended that the present invention be limited by the technique by which the operons are analyzed. In one embodiment, primers directed to these sequences can be employed in an amplification reaction (such as PCR). On the other hand, these conserved sequences can conveniently be analyzed with restriction enzymes. Specifically, the present invention contemplates digesting bacterial or fungal DNA with one or more restriction enzymes which will produce a piece of nucleic acid which is within (or bounded by) the 5' and 3' ends of the operon. The resulting digestion product will be conserved for any given species and can serve as a "signature" for that particular species (other species having one or more signature bands of a different size).

Specific embodiments of such a method include (but are not limited to) digestion with one or more restriction enzymes so as to produce any one of the following digestion products:

5'-16S-spacer-23S-spacer-5S-3',
5'-16S-spacer-23S-spacer-3',
5'-16S-spacer-23S-3',
5'-16S-spacer-3',
5'-16S-3',
5'-spacer-23S-spacer-5S-3',
5'-23S-spacer-5S-3',
5'-spacer-5S-3',
5'-5S-3',
5'-23S-3'
5'-spacer-23S-spacer-3', or
5'-spacer-23S-3'

The present invention also contemplates a host of variations on the above digestion products by cleaving in the middle of genes and/or in the middle of spacer regions. However, for the convenience of detecting such digestion products by gel electrophoresis, it is preferred that the digestion product (due to the relatively limited resolution level of gel electrophoresis) be at least 200 bp in size (and more preferably between 400 and 3000 bp in size).

In one embodiment, the present invention contemplates digestion of such DNA with restriction enzymes that cut only once in the DNA encoding 16S ribosomal RNA and only once in the DNA encoding 23S ribosomal RNA. In a preferred embodiment, the present invention contemplates digestion of bacterial DNA using a single restriction enzyme which cuts only once in the DNA encoding 16S ribosomal RNA and only once in the DNA encoding 23S ribosomal RNA.

In one embodiment, the present invention contemplates a method for bacterial speciation, comprising: i) isolation of bacterial DNA from a sample, said DNA comprising DNA encoding 16S and 23S rRNA; ii) digestion of said isolated DNA with one or more restriction enzymes under conditions such that restriction fragments are produced, said restriction fragments comprising a first digestion product of said DNA encoding 16S and 23S rRNA, said first digestion product comprising at least a portion of said DNA encoding 16S rRNA and at least a portion of said DNA encoding 23S rRNA; iii) separation of said restriction fragments (e.g. by gel electrophoresis), iv) detection of said first digestion product.

In another embodiment, the present invention contemplates a method for bacterial speciation, comprising: i) isolation of bacterial DNA from a sample; said DNA comprising DNA encoding 16S and 23S rRNA; ii) digestion of said isolated DNA with one or more restriction enzymes under conditions such that restriction fragments are produced, said restriction fragments comprising first and second digestion products (e.g. signature bands) of said DNA encoding 16S and 23S rRNA, said first digestion product being larger than said second digestion product, and comprising at least a portion of said DNA encoding 16S rRNA and at least a portion of said DNA encoding 23S rRNA; iii) separation of said restriction fragments (e.g. by gel electrophoresis), iv) detection of said first and second digestion products.

In yet another embodiment, the present invention contemplates a method for bacterial speciation, comprising: a) providing i) a first biological sample comprising bacterial DNA from a known bacterial species, and ii) a second biological sample comprising bacterial DNA from a bacterium whose species is unknown; b) isolating i) a first preparation of bacterial DNA from said first sample and ii) a second preparation of bacterial DNA from said second sample, said DNA of said first and second preparations comprising DNA encoding 16S and 23S rRNA; c) digesting, in any order, i) said first preparation of isolated DNA with one or more restriction enzymes under conditions such that a first preparation of restriction fragments are produced, said first preparation of restriction fragments comprising a first digestion product, said first digestion product comprising at least a portion of said DNA encoding 16S rRNA and at least a portion of said DNA encoding 23S rRNA, and ii) said second preparation of isolated DNA with one or more restriction enzymes under conditions such that a second preparation of restriction fragments are produced, said second preparation of restriction fragments comprising a second digestion product, said second digestion product comprising at least a portion of said DNA encoding 16S rRNA and at least a portion of said DNA encoding 23S rRNA; d) separating, in any order, i) said restriction fragments (e.g. by gel electrophoresis) from said first preparation, and ii) said restriction fragments (e.g. by gel electrophoresis) from said second preparation; and e) comparing of said first and second digestion products.

It is convenient to isolate bacterial DNA by lysis of bacteria to release DNA. It is also convenient to separate restriction fragments by gel electrophoresis, followed by transfer to a membrane for blotting with an oligonucleotide probe.

It is not intended that the present invention be limited by the nature of the sample. The terms "sample" and "specimen" in the present specification and claims are used in their broadest sense. On the one hand they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid (CSF), semen, and saliva, cells as well as solid tissue (including both normal and diseased tissue). These terms also refers to swabs and other sampling devices which are commonly used to obtain samples for culture of microorganisms. In addition, fluids such as IV fluids, water supplies and the like are contemplates as samples.

It is also not intended that the invention be limited by the particular purpose for carrying out the biological reactions. The present invention is applicable to medical testing, food testing, agricultural testing and environmental testing. In one medical diagnostic application, it may be desirable to simply detect the presence or absence of specific pathogens (or pathogenic variants) in a clinical sample. In yet another application, it may be desirable to distinguish one species or strain from another.

With regard to distinguishing different species, in one embodiment, the present invention contemplates comparing two samples suspected to be different species. In another embodiment, a species that is suspected to have changed or diverged from the parent species is compared with the parent species. For example, a species or strain of bacteria may develop a different susceptibilities to a drug (e.g. antibiotics) as compared to the parent species; rapid identification of the specific species or subspecies aids diagnosis and allows initiation of appropriate treatment.

It is not intended that the present invention be limited by the means of detection or the means of comparing first and second digestion products. In one embodiment, said digestion products that are separated by gel electrophoresis are probed with a labeled oligonucleotide in a hybridization reaction.

The present invention can be used with-particular success when comparing samples. In one embodiment, the present invention contemplates a method of analyzing nucleic acid in biological samples, comprising: a) providing: i) first and second samples comprising bacterial nucleic acid, ii) a restriction enzyme capable of generating a restriction fragment with (or bounded by) the 5' and 3' ends of a bacterial Ribosomal operon b) treating said nucleic acid of each of said two samples under conditions so as to produce restriction fragments; c) separating said restriction fragments; and d), comparing said restriction fragments from said first and second samples.

It is not intended that the present invention be limited by the number or nature of samples compared. Clinical, food, agricultural, and environmental samples are specifically contemplated within the scope of the present invention.

The present invention contemplates using restriction enzymes wherein the corresponding restriction enzyme recognition sequence exists only once in the 16s and 23s nucleic acid. Alternatively, restriction enzymes can be selected based on the known nucleic acid sequences (see e.g. FIGS. 4 and 6).

DEFINITIONS

To facilitate understanding of the invention, a number of terms are defined below.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

Prokaryotic ribosomes are constructed from 50S and 30S subunits that join together to form a 70S ribosome. The large subunit comprises a single "23S rRNA" molecule and a "5S rRNA" molecule, while the small subunit comprises a single "16S rRNA" molecule.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A."

Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

Ribosomal RNA molecules are characterized by the presence of numerous sequences that can form complementary base pairs with sequences located else where in the same molecule. Such interactions cause rRNA molecules to fold into three-dimensional configurations that exhibit localized double-stranded regions.

As used herein, the term "gene" means the deoxyribonucleotide sequences comprising the coding region and including sequences located adjacent to the coding region on both the 5' and 3' ends typically for a distance of about 1–3 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

The chromosomal DNA of prokaryotic cells contains multiple copies of the genes coding for rRNAs. For example, the bacterium *E. coli* contains seven sets of rRNA genes. In the rRNA transcription unit of *E. coli,* the three genes are typically arranged in the order 16S-23S-5S, with "spacer" DNA separating each gene (the spacer DNA separating 23S from 16S typically comprises one or more tRNA genes in addition to unencoded).

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding maybe tested by the use of a second target sequence which lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS; 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500nucleotides in length is employed.

Other equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency can be used (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0 t$ or $R_0 t$ analysis) or between one nucleic acid sequence present in solution and another nucleic acid sequence immobilized to a solid support [e.g., a nylon membrane or a nitrocellulose filter as employed in Southern and Northern blotting, dot blotting or a glass slide as employed in in situ hybridization, including FISH (fluorescent in situ hybridization)].

As used herein, the term "$T_m$" is used in reference to the "melting temperature." The melting temperature is the temperature at which a population of double-stranded nucleic acid molecules becomes half dissociated into single strands (the mid-point). The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl [see e.g., Anderson and Young, Quantitative Filter Hybridization, in *Nucleic Acid Hybridization* (1985)]. Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m - 5°$ C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out using polymerase chain reaction technologies well known in the art [Dieffenbach C W and G S Dveksler (1995) *PCR Primer, a Laboratory Manual*, Cold Spring Harbor Press, Plainview N.Y.]. As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

Amplification in PCR requires "PCR reagents" or "PCR materials", which herein are defined as all reagents necessary to carry out amplification except the polymerase, primers and template. PCR reagents normally include nucleic acid precursors (dCTP, dTTP etc.) and buffer.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligpnucleotide of interest. A probe may be single-stranded or double-stranded. Probes are useful in the detection, identification and isolation of particular gene sequences. It is contemplated that any probe used in the present invention will be labelled with any "reporter molecule," so that it is detectable using any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence. Such enzymes can be used to create Restriction Fragment Length Polymorphisms (RFLPs). RFLPs are in essence, unique fingerprint snapshots of a piece of DNA, be it a whole chromosome (genome) or some part of this, such as the regions of the genome that specifically flank ribosomal operons. All such RFLP fingerprints are indicative of the random mutations in all DNA molecules that inevitably occur over evolutionary time. Because of this, if properly interpreted, evolutionary relatedness of any two genomes can be compared based on the fundamental assumption that all organisms have had a common ancestor. Thus, the greater the difference in RFLP fingerprint profiles, the greater the degree of evolutionary divergence between them (although there are exceptions). With such an understanding, it then becomes possible, using appropriate algorithms, to covert RFLP profiles of a group of organisms (e.g. bacterial isolates) into a phylogenic (evolutionary) tree.

RFLPs are generated by cutting ("restricting") a DNA molecule with a restriction endonuclease. Many hundreds of such enzymes have been isolated, as naturally made by bacteria. In essence, bacteria use such enzymes as a defensive system, to recognize and then cleave (restrict) any foreign DNA molecules which might enter the bacterial cell (e.g. a viral infection). Each of the many hundreds of different restriction enzymes has been found to cut (i.e. "cleave" or "restrict") DNA at a different sequence of the 4 basic nucleotides (A, T, G, C) that make up all DNA molecules, e.g. one enzymes might specifically and only recognize the sequence A-A-T-G-A-C, while another might specifically and only recognize the sequence G-T-A-C-T-A, etc. etc. Dependent on the unique enzyme involved, such recognition sequences vary in length, from as few as 4 nucleotides (e.g. A-T-C-C) to as many as 21 nucleotides (A-T-C-C-A-G-G-A-T-G-A-C-A-A-A-T-C-A-T-C-G). From here, the simplest way to consider the situation is that the larger the recognition sequence, the fewer restriction fragments will result as the larger the recognition site, the lower the probability is that it will repeatedly be found throughout the genomic DNA.

In one embodiment, the present invention utilizes the restriction enzyme called EcoRI which has a 6 base pair (nucleotide) recognition site. Thus, given that there exist but 4 nucleotides (A,T,G,C), the probability that this unique 6 base recognition site will occur is $4^6$, or once in every 4,096 nucleotides. Given that the *H. influenzae* ("Hi") genome (chromosome) is approximately $2 \times 10^6$ bp (base pairs) in length, digestion of this DNA with EcoRI theoretically should yield 488 fragments. This varies significantly from isolate to isolate of *H. influenzae* because of "random mutations" that inevitably occurs over evolutionary time, some of which either destroy an EcoRI sequence cutting site, or create a new one. As such, the overall degree of variation in EcoRI RFLP profiles among a series of isolates within a given species such as *H. influenzae*, is indicative of the degree of genetic relatedness of these isolates (although there are exception). Using appropriate algorithms, such RFLP profiles are readily converted to "phylogenetic trees" (see e.g. FIG. 3) which are simply a diagrammatic figures indicating the evolutionary divergence of isolates from some theoretically common ancestor.

Once the genomic (chromosomal) DNA of a bacterial isolate has been isolated, it is then digested (cut) with an enzyme such as EcoRI. Following the digestion, the resultant individual fragments are separated from one another based on their sizes. This can be done by using agarose gel electrophoresis. In essence, during electrophoresis the smaller molecules (DNA fragments) move faster than larger one and thus the resultant separation is a gradient from the largest to the smallest fragments. These can easily be visualized as bands down the electrophoresis gel, from the top to the bottom with the smallest fragments bottom-most.

Using ribotyping methodology, DNA fragments involving the multiple (e.g. 6 for the case of *H. influenzae*, 7 for the case of *E. coli*, etc) ribosomal operons and the immediately flanking DNA sequences (genes) can be distinguished by hybridization of the resultant electrophoresis separated DNA fragments with a radioactively labeled ribosomal operon DNA probe. This then reduces the total number of visualized DNA fragments (predicted above to be approximately 488 restriction fragments) to those only including or immediately flanking the RNA operons, about 14 fragments in toto for *H. influenzae*. Nonetheless, because of inevitable random background mutation indicative of evolutionary time, with the exception of very recently evolved clones, every independent isolate of *H. influenzae* will have a variant EcoRI ribotype RFLP profile. And the more variant, the more distantly related will be any two isolates so compared. In contrast, rigorous conservation of 16S and 23S rRNA sequences makes possible the unique species-specific RFLPs produced according to the methods and compositions of the present invention.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand.

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligo-deoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists [J. Sambrook et al. (1989) *Molecular Cloning: A Laboratory Manual*, Cold Spring Harbor Press, N.Y., pp 9.31–9.58].

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligo-deoxyribonucleotide probe or DNA probe to detect RNA species complementary to the probe used. Northern blots are a standard tool of molecular biologists [J. Sambrook, J. et al. (1989) supra, pp 7.39–7.52].

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligo-ribonuclotide probe or RNA probe to detect DNA species complementary to the ribo probe used.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature.

As used herein, the term "purified" or "to purify" refers to the removal of undesired components from a sample.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables).

The term "bacteria" and "bacterium" refer to all prokaryotic organisms, including those within all of the phyla in the Kingdom Procaryotae. It is intended that the term encompass all microorganisms considered to be bacteria including Mycoplasma, Chiamydia, Actinomyces, Streptomyces, and Rickettsia. All forms of bacteria are included within this definition including cocci, bacilli, spirochetes, spheroplasts, protoplasts, etc. Also included within this term are prokaryotic organisms which are gram negative or gram positive. "Gram negative" and "gram positive" refer to staining patterns with the Gram-staining process which is well known in the art [Finegold and Martin, Diagnostic Microbiology, 6th Ed. (1982), C V Mosby St. Louis, pp 13–15]. "Gram positive bacteria" are bacteria which retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

DESCRIPTION OF THE DRAWINGS

FIG. 2 is an autoradiograph of EcoRI RFLPs of H. influenzae isolates from diverse sources, including the genomically sequenced strain Rd.

DESCRIPTION OF THE INVENTION

Figure 1:
FIG. 1 schematically shows the 6 Ribosomal operons of the genomically sequenced H. influenzae strain Rd.

The present invention relates to the identification of species, and in particular, methods and compositions for determining the species for an unknown bacterium (or fungus) in a sample. The methods and compositions of the present invention permit distinguishing between bacterial species (or between fungal species) and determining the identity of bacterial (or fungal) pathogens in biological samples. In one embodiment, the present invention contemplates the use of restriction enzymes followed by probing with an oligonucleotide capable of hybridizing to fragments comprising at least a portion of DNA encoding 16S and/or 23S rRNA. In this manner, the present invention applies, in one embodiment, the "discriminatory power" of the methodology of ribotyping to the speciation of microbes for the first time. The potential use of ribotyping as a method for speciation has been completely overlooked.

To date, ribotyping has been applied for the purpose of examining differences WITHIN a species. Specifically, ribotyping has been employed for the purpose of epidemiological 'typing' within a given species, where 'variability' of the ribotype RFLP profiles of individual isolates, one clinical isolate versus another clinical isolate, was of interest for intra-species discriminatory purposes (for example, to determine whether or not bacterial isolates within a known species were from an epidemic cluster involving a single clone spread among patients). As such, the conserved species-specific signature bands were not recognized as relevant. Instead, the variable bands making up the ribotype profile have been of interest for discriminatory epidemiological purposes and phylogenetic tree building.

The present invention, by contrast, generates a species-conserved set of RFLP bands, unique for each species. While of no interest for intra-species discrimination, these species conserved sets represent precise markers appropriate for inter-species discriminatory purposes (i.e. to determine per se, the species of a given, unknown isolate—which is a most needed assay in the clinical microbiology lab of a hospital). Since all bacterial species examined by the inventor display a conserved set of species-specific signature RFLP bands, unique for every species, Ribosomal operon-based discrimination of these unique species specific bands represents the most practical means available for speciation of bacteria (in that the method is less tedious and far more applicable—as compared to sequencing—to the clinical microbiology setting).

It must be stressed that the polymorphisms currently exploited in conventional, epidemiological and phylogenetic ribotyping are polymorphisms that are not directly related to ribosomal operon sequences. Rather, because of the conservation of DNA encoding 16s and 23s rRNA within any species, polymorphisms typically result from variation in closest flanking sequences (that is to say, nucleic acid falling outside of the region defined by: 5'-16S-spacer-23S-spacer-5S-3'). This point can be readily illustrated with the strain Hi Rd, because the complete chromosomal sequence of this strain is known. In this regard, it can be seen from FIGS. 1 and 2 that it is possible to predict the precise size of the 12 different flank sequences generated by an EcoRI digestion (or the fragments generated with any other restriction enzyme for that matter) of the 6 rrn operons of strain Rd. With such knowledge of the RFLP profile of the sequenced Hi strain Rd, using molecular genetic methods (such as hybridization), it is possible to precisely analyze any alterations from this prototypic ribotype fingerprint as found among other Hi isolates.

From this example with Hi, it should be clear that the polymorphisms generated by the conventional ribotyping technique have nothing directly to do with variability of Ribosomal operon sequences. Rather, these polymorphisms result from variations in the neutral genes that are genetically-linked to (i.e. that flank) the multiple ribosomal operons encoded by all bacterial chromosomes.

In constrast to conventional ribotyping, the present invention utilizes the Ribosomal operon sequences which vary less than 3% (and more preferably less than 2%) within a species but vary between species. The description of the invention involves the I) Preparation of Nucleic Acid from Samples; II) Selection of A Restriction Enzyme, III) Design of the Probe, IV) Comparing Biological Samples, and V) Speciation In A Clinical Setting.

I. The Preparation of Nucleic Acid

A. DNA Preparation

The nucleic acid content of cells consists of deoxyribonucleic acid (DNA) and ribonucleic acid (RNA). With respect to DNA preparation, a variety of preparation schemes are possible. Typically, the steps involved in purification of nucleic acid from cells include 1) cell lysis; 2) inactivation of cellular nucleases; and 3) separation of the desired nucleic acid from the cellular debris and other nucleic acid. Cell lysis may be achieved through various methods, including enzymatic, detergent or chaotropic agent treatment. Inactivation of cellular nucleases may be achieved by the use of proteases and/or the use of strong denaturing agents. Finally, separation of the desired nucleic acid can be achieved by extraction of the nucleic acid with solvents (e.g. phenol or phenol-chloroform); this method partitions the sample into an aqueous phase (which contains the nucleic acids) and an organic phase (which contains other cellular components, including proteins).

B. RNA Preparation

It is preferred that the present invention utilize DNA and restriction enzymes to analyze bacterial and fungal Ribosomal operon conserved sequences. On the other hand, such conserved sequences may also be examined in the form of 16S, 23S and/or 5S rRNA. For example, such rRNA may be used as template in a PCR reaction with primers (typically DNA primers) capable of amplying such rRNA.

It should be stressed, however, that the preparation of RNA is complicated by the presence of ribonucleases that degrade RNA (e.g., T. Maniatis et al., Molecular Cloning, pp. 188–190, Cold Spring Harbor Laboratory [1982]). Furthermore, the preparation of amplifiable RNA is made difficult by the presence of ribonucleoproteins in association with RNA. (See, R. J. Slater, In: *Techniques in Molecular Biology*, J. M. Walker and W. Gaastra, eds., Macmillan, N.Y., pp. 113–120 [1983]).

II. Selection Of A Restriction Enzyme

As noted above, the present invention contemplates in one embodiment that conserved sequences can conveniently be analyzed with restriction enzymes. Specifically, the present invention contemplates digesting bacterial or fungal DNA with one or more restriction enzymes which will produce a piece of nucleic acid which is within (or bounded by) the 5' and 3' ends of the Ribosomal operon. The resulting digestion product will be conserved for any given species and can serve as a "signature" for that particular species (other species having one or more signature bands of a different size).

A variety of restriction enzymes (and corresponding restriction sites) are contemplated. Given the sequence of the Ribosomal operon for any particular species, restriction enzymes can be selected on the basis of primary structure of the DNA. However, in a preferred embodiment, restriction enzymes are selected based on ultraconserved sequences within the Ribosomal operon; these sequences encode rRNA that takes part in the formation of secondary structures and are known to be more highly conserved because they must fold on themselves (forming secondary structures through Watson/Crick hydrogen bonding). Such sequences encoding rRNA involved in secondary structures are known for some organisms and can readily be determined from the primary structure of the ribosomal DNA for other species using commerically available computer programs.

III. Design of The Probe

In the nucleic acid hybridization step of the method of the present invention, the test DNA is denatured and exposed to denatured DNA of known sequence (i.e. "the probe") from a particular organism. The amount of hybridization between the test DNA and known DNA provides an indication of the degree of relatedness between the test and known organisms. An important drawback to this approach is that hybridization between two single DNA strands can occur even when 15% of the sequences are not complementary. Moreover, to identify appropriate restriction fragments, one must be able to identify restriction fragments that contain only very short regions (as short as 10 bases) of the 16s, 23s or 5S nucleic acid.

Regardless of these constraints, based on the knowledge of the specific Ribosomal operon DNA sequences of a particular species of bacteria which are recognized by particular restriction endonuclease ("RE"), the present invention contemplates a probe that can be designed to ensure a specific reaction.

The most general ribosomal RNA probe substrate applicable is obtained from purification of bulk ribosomal RNA (16S, 23S and 5S) molecules [See e.g. LiPuma-et al., *J. Pediatrics* 113:859 (1988)]. A more convenient approach is one using a cloned ribosomal operon which is then digested from the cloning vector, separated by electrophoresis, removed from the electrophoretic gel, and then used as probe substrate [see e.g. Arthur et al., Infection & Immunity 58:471 (1990)].

The present invention contemplates a variety of methods for labeling probes, including but not limited to isotopically labeling probes. In one embodiment, nick translation is employed. Briefly, the DNA is lightly "nicked" (single-stranded breaks) with DNAase, and a DNA polymerase which can displace strands at nicks polymerizes DNA using the strand that has not been displaced as template. The nucleoside triphosphates are tagged with isotopes (or other detectable groups) and the polymerase introduces such markers into the nicked DNA.

In another embodiment, the probe is made by random priming. Briefly, the DNA is denatured. Thereafter, small, random oligonucleotides, a labeled substrate, buffers and a DNA polymerase which has no 3'-OH editing function are added. The random oligonucleotides hybridize to places on the DNA and serve as primers for the synthesis of new, labeled DNA.

In yet another embodiment, the probe is end labeled. Briefly, either a kinase attaches a labeled phosphate to the 3'-OH of the DNA or a DNA polymerase with 3' editing function is forced to depolymerize from the 3' end; the resulting single-stranded DNA is used as a template to synthesize labeled DNA.

IV. Comparing Biological Samples

The present invention contemplates, in one embodiment, using electrophoresis to separate RFLP fragments for the comparison of the results between samples. Such an approach can utilize control samples or control fragments to ensure the identification of "signature bands" for a particular species. Moreover, it may be convenient to detect ONLY the signature bands; this can be done by a variety of methods, including but not limited to the isolating of the signature bands (i.e. free of other restriction fragments). Finally, it may be desirable to automate the analysis.

A. Control Samples

In one embodiment, the present invention contemplates a method wherein a sample of a known bacterial or fungal species is treated in parallel with the test sample(s). In such an approach, the known species is treated with the same restriction enzyme(s) and the resulting fragments are placed in a control lane of the gel, permitting comparison of fragments between the control samples and the test sample (s). Likewise the control may comprise other types or combinations of DNA fragments of known size extracted and prepared for this purpose.

B. Control Fragments

While treating a control sample in parallel is readily done, it may be more convenient to run pre-digested control bands along with the test sample(s). In such a case, the restriction fragments from the pre-digested known sample are simply added to a control lane at the time the test samples have been processed to make them ready for gel electrophoesis.

C. Detecting ONLY The Signature Bands

It may be convenient to detect ONLY the signature bands when comparing samples. This can be done by a variety of methods, including but not limited to the isolating of the signature bands (i.e. free of other restriction fragments). In one embodiment, the present invention contemplates using electrophoresis in combination with a means for sizing the fragment (e.g. HPLC or Mass Spectrometry). In such an approach, restriction enzymes can be utilized that generate the smallest fragment so that this fragment (or fragments) will elute from bottom of the gel prior to the other fragments. The eluted fragment can immediately be examined for size to confirm that the signature band is present or absent in the test sample.

Similarly, the gel for gel electrophoresis can be prepared so as to permit the separation of only fragments in the size range of the signature bands. For example, larger bands capable of hybridizing to the probe would remain at the top of the gel (or be only poorly resolve near the top of the gel).

Also, PCR amplification based on primers including a known restriction site in the conserved region followed by hybridization can be employed.

D. Automation

The present invention contemplates the automation of analysis. In this regard, the present invention specifically contemplates the utilization of the Qualicon (a Dupont subsidiary) "RiboPrinter System"—which is a fast automated apparatus that is (with some modifications, including but not limited to, the provision of marker DNA comprising signature bands) amenable to the automation of some of the above-described methods. In operation, single colonies from 8 unknown microbes are inoculatd directly into a sample carrier into which a "DNA pre pack" is added that contains lysis buffer (enzymes to break open bacteria, along with restriction endonucleases for cutting genomic DNA, along with marker DNA molecules for comparative sizing of RFLP profiles). After initial heat inactivation of colonies, followed by cell lysis and restriction of the DNA, the DNA is then automatically extracted and restriction fragments separated according to size by gel electrophoresis, and then transferred to a hybridization membrane. DNA is then automatically hybridized to a labeled ribosomal operon probe, after which a chemiluminescent agent is introduced. Emission of light from hybridized fragments is captured by digitizing camera and stored as image data. Using proprietary algorithms, a RiboPrint pattern for each sample is extracted from the image data. This pattern can then be compared to other RiboPrint RFLP profiles stored in the system. Such results can be generated every 8 hours, with analysis of the next set of 8 samples begun 2 hours after the first.

The present invention also contemplates a new means for resolving species specific ribosomal RNA bands. This involves hybridization in solution following restriction digestion of the unknown chromosomal DNA sample after which unbound chemiluminescent probe is removed and the sample is electrophoresed. At this point, based on the known rate of migration of DNA fragments of variant size, a chemiluminescent detector is used to detect when hybridized restriction fragments chemilumiescently labeled with the rrn probe elute from the electrophoretic gel. Given the elution rate will be determined by speed of migration, and that migration speed for a fragment of a given size is predictable, the time at which the so chemilumiescently labeled hybridized fragment elutes will indicate its size and thus reveal the signature bands indicative of one species or another.

V. Speciation In A Clinical Setting

The present invention specifically contemplates applying the above-described method to medical diagnostic applications. For example, it may be desirable to simply detect the presence or absence of specific pathogens (or pathogenic variants) in a clinical sample. In yet another application, it may be disirable to distinguish one species from another. This is a process carried out tens of thousands of times daily in clinical medical microbiology laboratories in hospitals throughout the world, albeit without the benefit of the present invention. Indeed, it is the most common diagnostic analysis (test) carried out in the hospital clinical microbiology laboratory.

Identification of a particular species of microbe causing the infection of a particular patient is needed in order to decide how to treat the infection, e.g. what type of antibiotic should be used since different species (e.g. *E. coli* versus *Pseudomonas aeruginosa* versus *Haemophilus influenzae* versus *Burkholderia cepacia*) exhibit different profiles of sensitivity versus resistance to the same antibiotic. Likewise speciation may reveal whether there exists a pathogen expressing tissue-damaging toxins.

Currently, speciation is most typically accomplished in the hospital clinical microbiology lab using a combination of phenotypic assays involving: (i) a series of 10–15 biochemical tests for nutrients required and substrates metabolized or catabolizedby microbes); (ii) growth on selective growth media, and (iii) others. At best, results from such tests typically take 12–24 hours to obtain and sometimes as long as 5 days (by which time many an infected patient has expired). Such test decipher the species involved with approximately 95% of clinical samples.

The present invention, as noted above, contemplates a non-sequencing approach to speciation. This is because an approach involving sequencing (e.g. purification of DNA, PCR amplification of the 16S gene of the ribosomal operon followed by DNA sequencing) is complex, costly and labor intensive. A sequencing approach is likely to be unsuitable to the hospital setting.

That is not to say, however, that sequencing is altogether inappropriate in all settings. For example, when the 16S genes of different species are compared (e.g. *E. coli* versus *H. influenzae* versus *Neisseria meningitidis* versus *Streptococcus pneumoniae* versus *Staphylococcus aureus*, etc), greater than 10%–15% differences in the 16S genes are revealed. Given such large differences, it is possible to precisely identify the species of microbe in which the gene was found based on such sequencing of the 16S gene DNA.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); gm (grams); mg (milligrams); μg (micrograms); L (liters); ml (milliliters); μl (microliters); cm (centimeters); mm (millimeters); μm (micrometers); nm (nanometers); °C. (degrees Centigrade); Ci (Curies); EDTA (ethylenediamine-tetracetic acid); PAGE (polyacrylamide gel electrophoresis); bp (base pair); CPM (counts per minute).

The present invention is applicable to over 20 other species of bacteria: To prepare bacterial DNA, cells were pelleted from 5 ml overnight culture, washed with 50:20 mM TE buffer [50 mM Tris (pH 8.0), 20 mM EDTA (pH 8.0)) and re-dissolved in 4 ml 50:2 mM TE buffer (50 mM Tris (pH 8.0), 2 mM EDTA (pH 8.0)]. Cells were first incubated with 50 μl lysozyme solution (20 mg/ml) at 4° C. for 30 minutes and then incubated with 50 μl proteinase K (20 mg/ml) and 300 μl 10% SDS at 55° C. for 5 hours. 1 ml 10% lauroyl sarcosine (acid free) was added to the cell lysate, and the DNA was purified by equilibrium centrifugation in a caesium chloride-ethidium bromide gradient.

Restriction fragment length polymorphism (RFLP) associated with multicopy ribosomal operons was analysed using an rrnB probe. For southern blot analysis, the gel was transferred to a nitrocellulose membrane using a Bio-Rad vacuum blotting apparatus. DNA hybridisation procedure was as follows: After Southern blotting, the membrane was baked at 80° C. for 30 minutes, placed in a heat-sealable bag with 10–50 ml prehybridisation buffer, heat-sealed and then incubated at 42° C. for 5 minutes. Radio-labelled probe was prepared by adding: 32 μls DNA (DNA sample was a fragment cut from a LMP Agarose gel, and initially boiled for 10 min. before using), 10 μls OLB, 2 μls BSA, 5 μs $^{32}$P, 2 μls Klenow. Stock was 0.5 mCu in 50 ml (5 ml=50 mCu). The mixture was incubated for ~5 hours or overnight, in 37° C. H$_2$O bath. Before adding the probe to the blotted nitrocellulose membrane it was boiled for 10 minutes. Tracking dye was added to the DNA probe before boiling. The labelled probe was added to the membrane using a syringe. The bag was resealed and incubated at 42° C. for 4–24 hours on a shaker. The membrane was washed repeatedly but not allowed to dry. Autoradiography was then carried out.

EXAMPLE 1

Conserved, Species-specific Signature Bands: Novel Genetic Markers for Inter-species Discrimination for *H. influenzae*

Availability of the complete sequence of the chromosome of the *Haemophilus influenzae* ("Hi") strain Rd allowed us to predict a priori the resultant EcoRI RFLP profile generated from the known 6 rrn (ribosomal operon) of this strain. As shown in FIG. 1, with EcoRI sites occurring once each, in species-conserved 16S and 23S rrn gene sequences of each rrn operon, two possible internal fragments (16S-spacer-23S) are generated depending on presence or 1 or 2tRNA sequences within the spacer region between 16S and 23S genes. These two conserved EcoRI fragments (1,503 bp and ~1,748 bp) are found among all Hi isolates.

Among the >400, putative typable and "NT" (non-typable, i.e. unencapsulated) Hi isolates (see Table 1) examined by EcoRI ribotyping (FIG. 3), all serotype "a" through "e"RFLP profiles and 253 of 311 NTHi (non-typable Hi) RFLP profiles contained both signature bands. 53 NTHi RFLP profiles lacked both signature bands,whereas four lacked the 1748 bp signature band and 1 lacked the 1503 bp signature band. All serotype "f" RFLP profiles lacked both signature bands. These 58 NT and 8 serotype f isolates lacking EcoRI ribotype signature bands appear not to be members of the species *H. influenzae* but appear to be a new subspecies or species.

Figure 3:
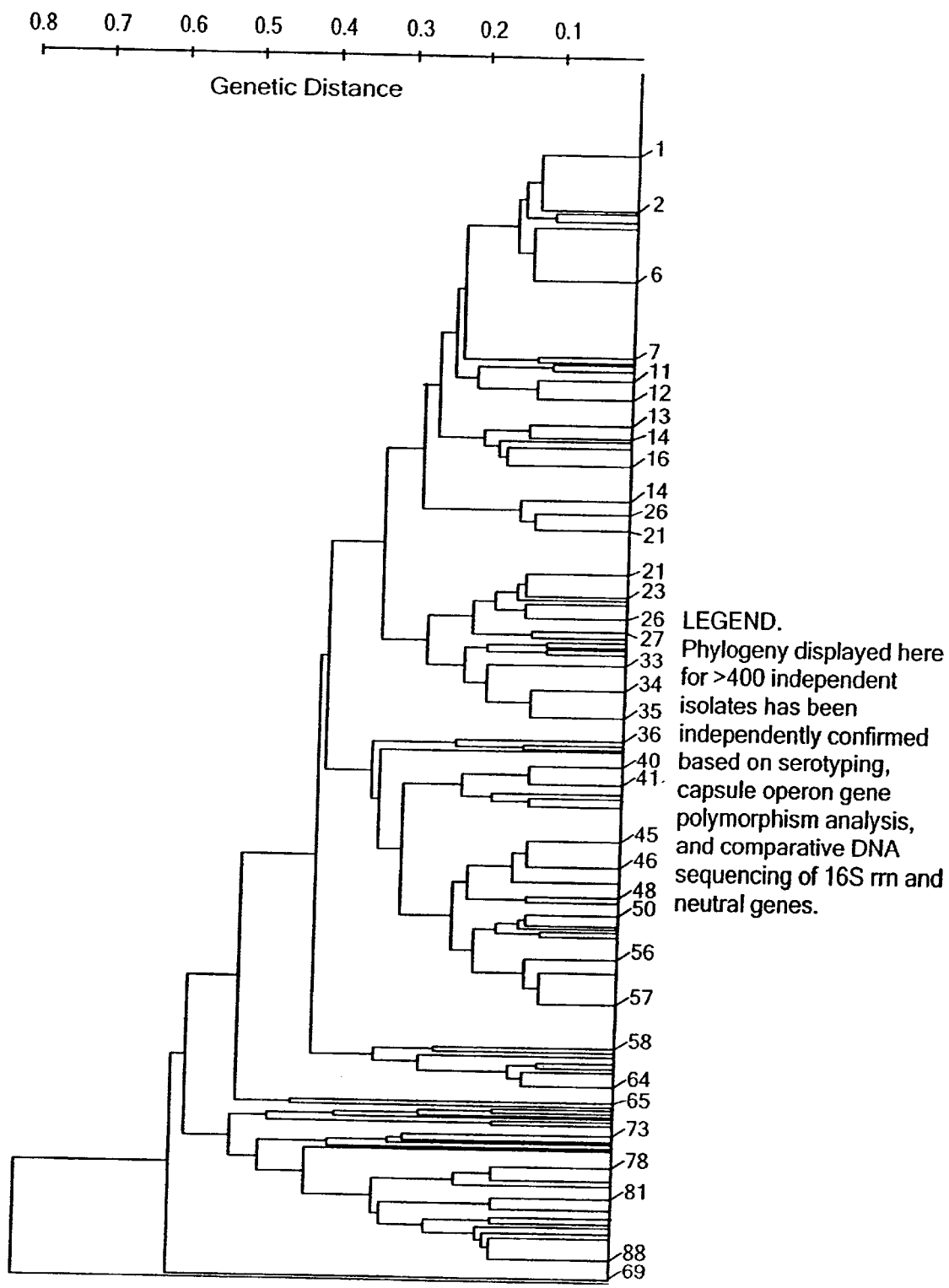
FIG. 3 is an EcoRI based phylogenic tree of a diverse collection of H. influenzae isolates (type "a" through "f", and non-typeable) from variant clinical and environmental sources and geographical locales, showing the signature bands of H. influenza with this restriction enzyme.

As described above, all 8 serotype "f" isolates plus 55 of 58 NTHi Isolates lacking one or more species specific EcoRI signature bands appear clustered together in the FIG. 3 dendrogram (the phylogenic tree) as a clearly distinct lineage(s) from all of the other EcoRI signature band-containing isolates, both serotype "a" through "e" and NT. The branches in the FIG. 3 dendogram are representative of the respective serotypes as follows:

Type "a" is represented by branches 22–26.

Type "b" is represented by branches 29–35.

Type "c" is represented by branches 50–54.

Type "d" is represented by branches 22–28.

Type "e" is represented by branches 58–64.

Type "f" is represented by branches 73–88 (comprising a unique lineage).

Based on methods known in the art, such as multi-locus enzyme electrophoresis (MLEE), this was not revealed in previous phylogenetic analyses of *H. influenzae*. Preliminary 16S rrn gene sequencing has confirmed that putative Hi isolates missing the EcoRI ribotype species-specific signature band(s) appear to have been mistyped as Hi by clinical microbiology labs providing these isolates.

EXAMPLE 2

Conserved, Species-specific Signature Bands: Novel Genetic Markers for Inter-species Discrimination for *E. coli*

Figure 4:
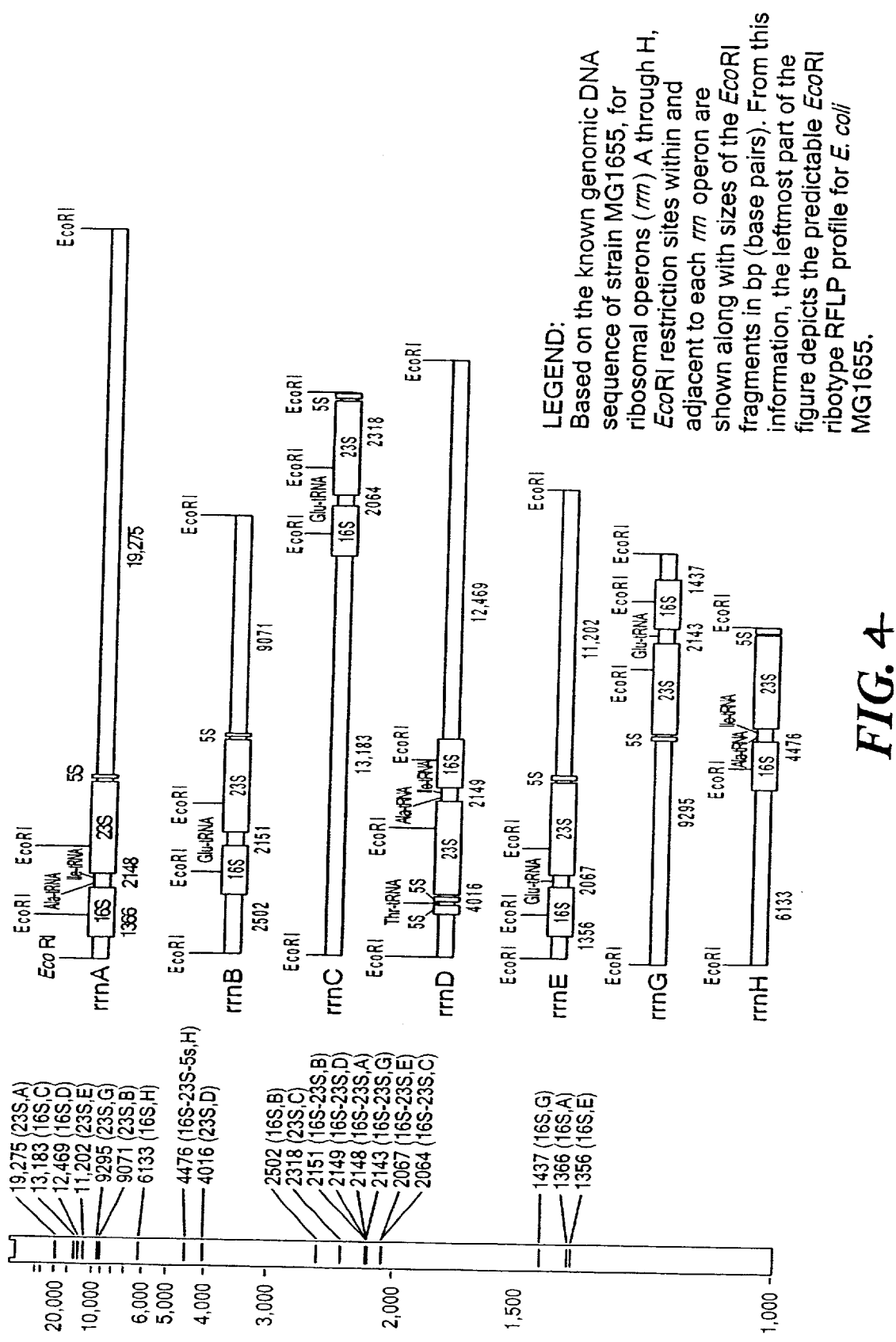
FIG. 4 shows the ribosomal operons of the genomically sequenced E. coli strain MG 1655.
Figure 5:
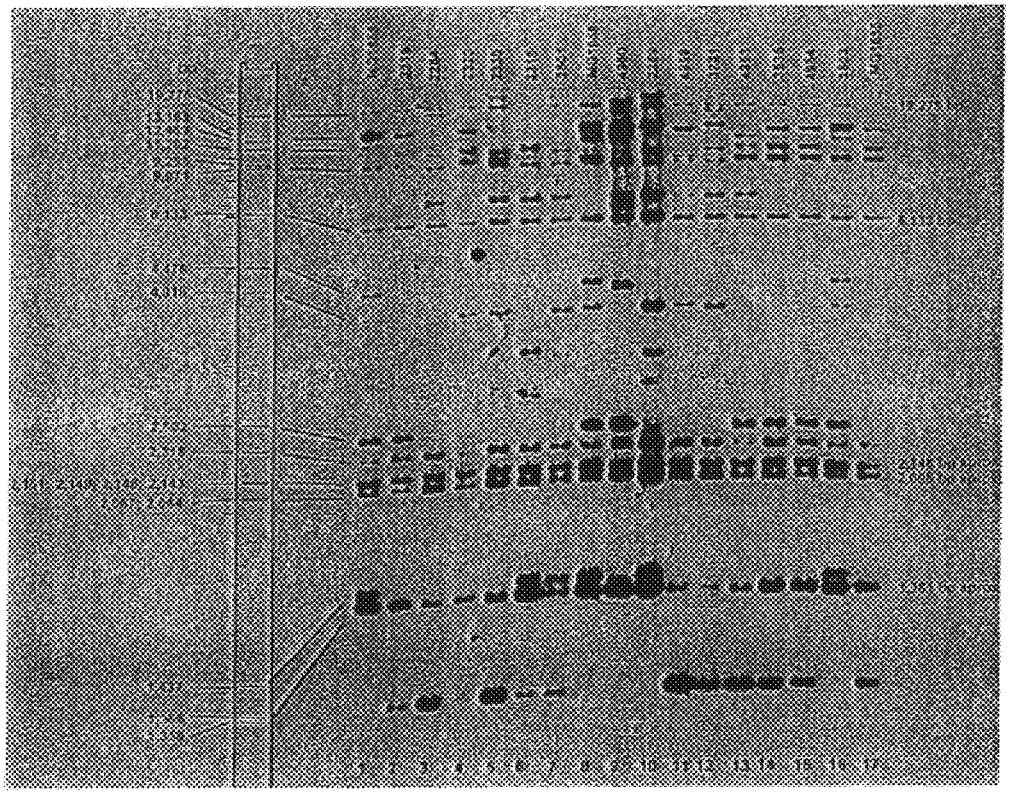
FIG. 5 is an autoradiograph of the EcoRI RFLPs of E. coli isolates from diverse sources, including the genomically sequenced strain MG 1655, showing the signature bands for this species using this restriction enzyme.

An analogous experiment to the *H. influenzae* Example 1 shown above is performed with the species *Escherichia coli*. In this experiment, the computer analysis exemplified by Example 1 for *H. influenzae* is utilized for the complete genomic sequence of the *E. coli* isolate MG 1655 [Blattner, F., Plunkett III, G., Bloch, C., Perna, N., Burland, V., Riley, M. The complete genome sequence of *Escherichia coil* K-12. Science 277 (5331), 1453–1462 1997]. Roughly 160 independently isolated *E. coli* strains from diverse geographical locales. and time periods and sources are analysed (representative data is shown in FIG. 5). In this case, the conserved EcoRI ribotype RFLP bands indicative of species *E. coli* were resolved to be 2.2 Kb in size. The inventor performed the sequence analyses for all seven (7) ribosomal operons (rrnA–rrnH) of the *E. coli* strain, looking for appropriately conserved restriction endonuclease sites, preferably one each in 16S and 23S RNA genes. A single site for EcoRI was found in the 16S region, and also a single EcoRI site was found in the 23S region (FIG. 4). Sizes of the signature bands of the ribosomal operons in bp are as follows:

2148 bp (rrnA);

2151 bp (rrnB);

2064 bp (rrnC)

2149 bp (rrnD);

2067 bp (rrnE);

2143 bp (rrnG);

4476 bp (rrnH).

Knowing the base pair numbers allowed for a priori prediction of the EcoRI ribotype RFLP profile of the genomically sequenced E. coli isolate MG1655. Also, this allowed for the prediction of the conserved, species specific bands represented by the internal fragments between the 16S and 23S EcoRI cut sites (FIG. 5).

Both the E. coli MG1655 strain and other 168 E. coli isolates were then tested to determine the genetic diversity. What was found here is variability in ribotype RFLPs with exception of the two conserved EcoRI bands. These two conserved EcoRI bands make up the EcoRI species specific signature.

Among the 185 putative isolates for this study, some were missing the bands that otherwise always clustered around the 2.2 Kb marker (i.e. the 2,065.5 and 2,148 bp bands). The isolates were re-typed (re-speciated) by the clinical microbiology lab. In every case, those isolates missing the 2 EcoRI RFLP bands proved NOT to be E. coli.

EXAMPLE 3

Figure 6:
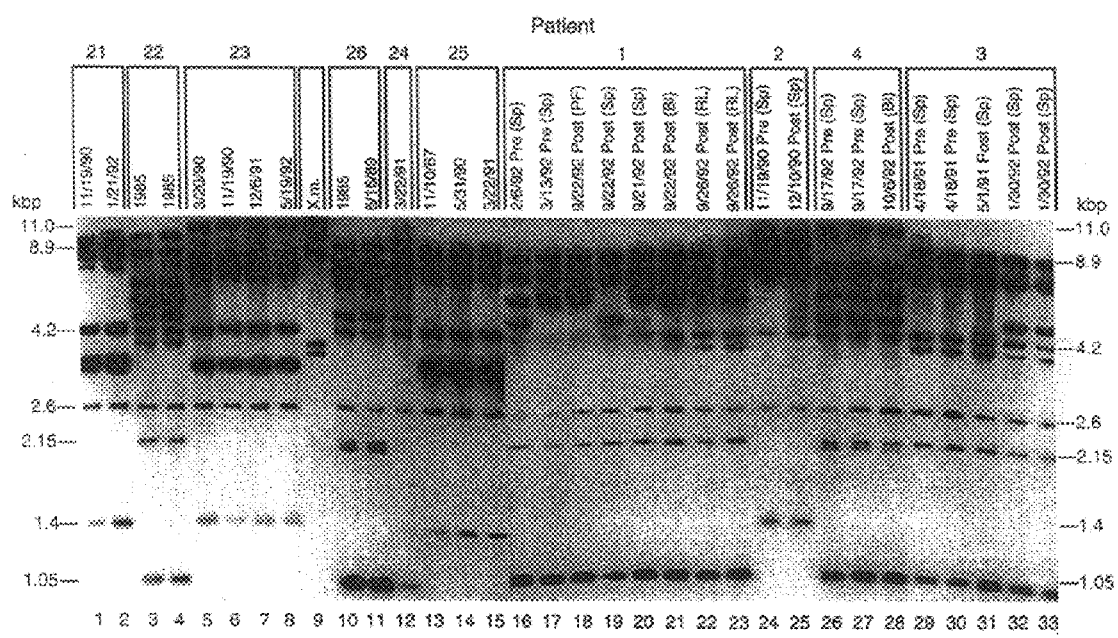
FIG. 6 is an autoradiograph of RFLP data for B. cepacia, showing signature bands for this species.

Conserved, Species-specific Signature Bands:
Novel Genetic Markers for Intra-species
Discrimination for B. cepacia An analogous experiment to Examples 1 and 2 shown above was performed with the species *Burkholderia cepacia*. Only in this case, the conserved EcoRI ribotype RFLP bands indicative of species *B. cepacia* were resolved to be 4.2 and 2.6 Kb in size (FIG. 6). And, as with *E. coli*, whenever an EcoRI ribotype characterized isolate in this *B. cepacia* study was found to be missing these RFLP bands, and subsequently examined by the clinical microbiology lab for speciation, it proved NOT to be in the *B. cepacia* species. One of these mis-typed non-cepacia isolates is shown in lane 9 of FIG. 6. It can be seen here that this isolate is missing the predictable *B. cepacia* species specific EcoRI ribotype bands at 4.2 and 2.6 Kb in size. This isolate proved to be another species, *Xanthomonas maltophilia*.

EXAMPLE 4

Comparison of Signature Bands

In this example, the specific signature bands were compared across the species tested in Examples 1, 2 and 3 above. When comparing the signature bands for *E. coli* versus *B. cepacia* (see FIGS. 5 and 6) as well as those for Hi verus *E. coli* versus *B. cepacia* (see FIG. 3), it is clear that these "signature" bands can be used to distinguish one species from another.

TABLE 1

| Lineage | Strain | Sero-type | Infection | Geographic location | Year |
|---|---|---|---|---|---|
| 1 | N-F433 | nt | Ear | Finland | 1995 |
| | N-F916 | nt | Ear | Finland | 1995 |
| | N-F402 | nt | Ear | Finland | 1995 |
| | N-F432 | nt | Ear | Finland | 1995 |
| | N-F354 | nt | Ear | Finland | 1995 |
| | N-F374 | nt | Ear | Finland | 1995 |
| | N-F375 | nt | Ear | Finland | 1995 |
| | N-F401 | nt | Ear | Finland | 1995 |
| | N-F1151 | nt | Ear | Finland | 1995 |
| | N-F1152 | nt | Ear | Finland | 1995 |
| | N-F1073 | nt | Ear | Finland | 1995 |
| | N-F1074 | nt | Ear | Finland | 1995 |
| | N-F1247 | nt | Ear | Finland | 1995 |
| | N-F1411 | nt | Ear | Finland | 1995 |
| | N-F164 | nt | Ear | Finland | 1994 |
| | N-F233 | nt | Ear | Finland | 1994 |
| | N-A14 | nt | Ear | Cleveland, OH | 1986 |
| | N-A1484A | nt | Blood | Connecticut | 1980's |
| | b-EOT81 | b | Epiglottis | Ottawa, Ont. | 1985–87 |
| | d-ELO127 | d | Ear | London, Ont. | 1985–87 |
| | ND8-1468 | nt | | | |
| | ND9-1200 | nt | Res | Los Angeles, CA | 1995 |
| | N-EA70 | nt | Sputum | Montreal, Que | 1985–87 |
| | N-ELO147 | nt | Sputum | London, Ont. | 1985–87 |
| | N-A15 | nt | Ear | Cleveland, OH | 1986 |
| | N-A32 | nt | Ear | Cleveland, OH | 1984 |
| | N-ESJ209 | nt | CSF | Montreal, Que. | 1985–87 |
| | N-F1003 | nt | Ear | Finland | 1995 |
| | N-F1004 | nt | Ear | Finland | 1995 |
| | N-F1042 | nt | Ear | Finland | 1995 |
| | ND21-1328 | nt | | | |
| | ND23-1109 | nt | Res | Hartford, CT | 1995 |
| | ND171182 | nt | Res | Phoenix, AZ | 1995 |
| | ND21038 | nt | CSF | Detroit, MI | 1995 |
| | ND10-238 | nt | Res | Clackamas, OR | 1994 |
| | ND11086 | nt | Ear | Cleveland, OH | 1995 |

TABLE 1-continued

| Lineage | Strain | Serotype | Infection | Geographic location | Year |
|---|---|---|---|---|---|
|  | ND111123 | nt | Res | Stanford, CA | 1995 |
|  | ND17-783 | nt |  |  |  |
|  | ND27-1433 | nt |  |  |  |
|  | ND27-999 | nt |  |  |  |
|  | ND231110 | nt | CSF | Hartford, CT | 1995 |
|  | ND241019 | nt | Res | Rochester, NY | 1995 |
|  | ND271007 | nt | Res | Worcester, MA | 1994 |
|  | ND28-10 | nt | Res | New York, NY | 1994 |
|  | ND28278 | nt | Res | New York, NY | 1994 |
|  | ND7-1526 | nt |  |  |  |
| 2 | N-F1363 | nt | Ear | Finland | 1995 |
| 3 | ND131158 | nt | Ear | Houston, TX | 1995 |
| 4 | b-B1324 | b |  |  | 1984 |
|  | N-EF147 | nt | Sputum | Halifax, NS | 1985–87 |
|  | N-EOT14 | nt | Epiglottis | Ottawa, Ont. |  |
|  | ND41093 | nt | Res | Rochester, NY | 1994 |
| 5 | ND41094 | nt | Res | Rochester, NY | 1994 |
| 6 | ND171184 | nt | Res | Phoenix, AZ | 1995 |
|  | ND171186 | nt | Res | Phoenix, Az | 1995 |
|  | ND131157 | nt | Res | Houston, TX | 1995 |
|  | ND171183 | nt | Res | Phoenix, AZ | 1995 |
|  | ND10-239 | nt | Res | Clackamas, OR | 1994 |
|  | ND111124 | nt | Res | Stanford, CA | 1995 |
|  | ND12-1119 | nt | CSF | Seattle, WA | 1995 |
|  | ND13-112 | nt | Res | Houston, TX | 1994 |
|  | N-F567 | nt | Ear | Finland | 1995 |
|  | N-F570 | nt | Ear | Finland | 1995 |
|  | N-F51 | nt | Ear | Finland | 1994 |
|  | N-F54 | nt | Ear | Finland | 1994 |
|  | N-F608 | nt | Ear | Finland | 1995 |
|  | N-F699 | nt | Ear | Finland | 1995 |
|  | N-F732 | nt | Ear | Finland | 1995 |
|  | ND10-189 | nt | Res | Clackamas, OR | 1994 |
|  | b-EA163 | b | Sputum | Montreal, Que. | 1985–87 |
|  | b-EE184 | b | CSF | Winnipeg, Man. | 1985–87 |
|  | ND91197 | nt | Res | Los Angeles, CA | 1995 |
|  | ND3110 | nt | Res | Evanston, IL | 1994 |
|  | ND9-1196 | nt | Res | Los Angeles, CA | 1995 |
|  | ND18174 | nt | Res | Chapel, NC | 1994 |
|  | ND221154 | nt | Res | Boston, MA | 1995 |
|  | ND27-1354 | nt |  |  |  |
|  | ND31031 | nt | Res | Evanston, IL | 1995 |
|  | N-F1015 | nt | Ear | Finland | 1995 |
|  | N-F1158 | nt | Ear | Finland | 1995 |
|  | N-A7 | nt | Ear | St. Louis, MO | 1985 |
|  | N-EF79 | nt | Bronchoscopy | Halifax, NS | 1985–87 |
|  | N-A1276 | nt | Blood | St Louis, MO | 1980's |
|  | N-A1328 | nt | Blood | St Louis, MO | 1980's |
|  | N-A1636 | nt | Blood | St. Louis, MO | 1980's |
|  | N-A3247A | nt | Ear | Cleveland, OH | 1980's |
|  | N-F1440 | nt | Ear | Finland | 1995 |
|  | N-F187 | nt | Ear | Finland | 1994 |
|  | N-F1159 | nt | Ear | Finland | 1995 |
|  | N-F1382 | nt | Ear | Finland | 1995 |
|  | N-F188 | nt | Ear | Finland | 1994 |
|  | N-F258 | nt | Ear | Finland | 1994 |
|  | N-F261 | nt | Ear | Finland | 1994 |
|  | N-F279 | nt | Ear | Finland | 1994 |
| 7 | N-A49 | nt | Blood | St. Louis, MO | 1995 |
| 8 | N-A1509 | nt | Ear | Philadelphia, PA | 1980's |
|  | N-A1512A | nt | Ear | Philadelphia, PA | 1980's |
| 9 | b-B7109 | b | Nasal | Stockholm | 1985 |
| 10 | ND41101 | nt | Res | Rochester, NY | 1994 |
| 11 | a-ELO16 | a | Eye | London, Ont. | 1985–87 |
|  | f-EF136 | f | Sputum | Halifax, NS | 1985–87 |
|  | ND231115 | nt | Res | Hartford, CT | 1995 |
|  | N-A12 | nt | Ear | Cleveland, OH | 1985 |
|  | ND21041 | nt | CSF | Detroit, MI | 1995 |
| 12 | N-F1146 | nt | Ear | Finland | 1995 |
|  | N-F1200 | nt | Ear | Finland | 1995 |
|  | ND9-1201 | nt | SA | Los Angeles, CA | 1995 |
|  | N-F1268 | nt | Ear | Finland | 1995 |
|  | N-F84 | nt | Ear | Finland | 1994 |
|  | ND1-1080 | nt | Res | Cleveland, OH | 1995 |
|  | ND241026 | nt | Res | Rochester, NY | 1995 |

TABLE 1-continued

| Lineage | Strain | Sero-type | Infection | Geographic location | Year |
|---|---|---|---|---|---|
| 13 | a-EC195 | a | Nasopharynx | Regina, Sask. | 1985–87 |
| | N-A1635 | nt | Blood | St. Louis, MO | 1980's |
| | ND9-1199 | nt | SA | Los Angeles, CA | 1995 |
| | ND271002 | nt | Res | Worcester, MA | 1994 |
| | ND9-1194 | nt | Res | Los Angeles, CA | 1995 |
| | N-EA145 | nt | Sputum | Montreal, Que. | 1985–87 |
| | ND21-1206 | nt | Res | Mobile, AL | 1995 |
| | ND23-938 | nt | | | |
| | ND231108 | nt | Res | Hartford, CT | 1995 |
| 14 | ND271003 | nt | BF | Worcester, MA | 1995 |
| 15 | ND271005 | nt | Res | Worcester, MA | 1994 |
| 16 | ND211208 | nt | Res | Mobile, AL | 1995 |
| 17 | N-A30 | nt | Ear | Cleveland, OH | 1983 |
| 18 | a-B6059 | a | Sputum | Newcastle, UK | 1964 |
| | a-B6064 | a | Sputum | Newcastle, UK | 1966 |
| | ND9-1195 | nt | Res | Los Angeles, CA | 1995 |
| | ND41098 | nt | Res | Rochester, MN | 1994 |
| | ND41100 | nt | BF | Rochester, MN | 1994 |
| | ND10241 | nt | Res | Clackamas, OR | 1994 |
| | ND111122 | nt | Res | Stanford, CA | 1995 |
| | N-F1124 | nt | Ear | Finland | 1995 |
| | ND10187 | nt | Res | Clackamas, OR | 1994 |
| | ND271004 | nt | CSF | Worcester, MA | 1994 |
| | ND28-13 | nt | Res | New York, NY | 1994 |
| | ND3111 | nt | Res | Evanston, IL | 1994 |
| | ND41096 | nt | Res | Rochester, MN | 1994 |
| 19 | a-B6062 | a | Nasal | Newcastle, UK | 1965 |
| | c-EC181 | c | Sputum | Regina, Sask. | 1985–87 |
| | ND271000 | nt | Res | Worcester, MA | 1994 |
| | N-F979 | nt | Ear | Finland | 1995 |
| | N-F981 | nt | Ear | Finland | 1995 |
| | N-A28 | nt | Ear | Cleveland, OH | 1983 |
| | N-F1071 | nt | Ear | Finland | 1995 |
| | N-F241 | nt | Ear | Finland | 1994 |
| | N-F253 | nt | Ear | Finland | 1994 |
| 20 | ND21036 | nt | CSF | Detroit, MI | 1995 |
| 21 | ND12-1117 | nt | CSF | Seattle, WA | 1995 |
| | ND3109 | nt | Res | Evanston, IL | 1994 |
| | N-F639 | nt | Ear | Finland | 1995 |
| | ND10-240 | nt | Res | Clackamas, OR | 1994 |
| | d-EOT156 | d | Eye | Ottawa, Ont. | 1985–87 |
| | N-A1515 | nt | Ear | Philadelphia, PA | 1980's |
| | a-EI111 | a | Bronchoscopy | Ste.-Foy, Que. | 1985–87 |
| | c-EC86 | c | Ear | Regina, Sask. | 1985–87 |
| | N-A26 | nt | Ear | Cleveland, OH | 1982 |
| | N-A27 | nt | Ear | Cleveland, OH | 1982 |
| | N-EF105 | nt | Sputum | Halifax, NS | 1985–87 |
| | N-ESJ136 | nt | Ear | Montreal, Que. | 1985–87 |
| 22 | N-F1542 | nt | Ear | Montreal, Que. | 1985–87 |
| | ND241023 | nt | Blood | Rochester, NY | 1995 |
| | N-F1396 | nt | Ear | Finland | 1995 |
| | N-F1541 | nt | Ear | Finland | 1996 |
| | N-F1233 | nt | Ear | Finland | 1995 |
| | N-F1241 | nt | Ear | Finland | 1995 |
| | N-F1275 | nt | Ear | Finland | 1995 |
| | N-F1345 | nt | Ear | Finland | 1995 |
| | a-B7190 | a | CSF | Malaysia | 1973 |
| | d-B6137 | d | Throat | Newcastle, UK | 1963 |
| | ND271009 | nt | Res | Worcester, MA | 1994 |
| | N-F1125 | nt | Ear | Finland | 1995 |
| | N-F1142 | nt | Ear | Finland | 1995 |
| | N-F1207 | nt | Ear | Finland | 1995 |
| | N-F1209 | nt | Ear | Finland | 1995 |
| 23 | a-B7032 | a | CSF | Papua New Guinea | |
| 24 | ND171189 | nt | Res | Phoenix, AZ | 1995 |
| 25 | a-B6069 | a | Throat | Newcastle, UK | 1962 |
| | a-B7115 | a | | Santo Domingo | |
| 26 | a-B7421 | | Nasal | Kenya | |
| | d-B1168 | d | | Massachusetts | 1983 |
| | a-B1042 | a | CSF | Arizona | 1981 |
| | a-B7031 | a | CSF | Papau New Guinea | |
| | d-B6150 | d | Sputum/blood | Kent, UK | 1985 |
| | d-B7033 | d | Blood | Papua New Guinea | |
| | Rd-ATCC51907 | | | | |
| | Rd-RM118 | | | | |
| 27 | d-ATCC9332 | | | | |

TABLE 1-continued

| Lineage | Strain | Sero-type | Infection | Geographic location | Year |
|---|---|---|---|---|---|
| 28 | N-ELO79 | nt | CSF | London, Ont. | 1985–87 |
|  | N-OT9 | nt | CSF | Ottawa, Ont. | 1985–87 |
| 29 | b-EA122 | b | CSF | Montreal, Que. | 1985–87 |
|  | N-F206 | nt | Ear | Finland | 1994 |
| 30 | b-ATCC9795 |  |  |  |  |
| 31 | b-B8069 | b | Blood | Knots Landing | 1985 |
| 32 | b-CMINNA | b |  | Minnasota |  |
| 33 | ND1-1079 | nt | Res | Cleveland, OH | 1995 |
|  | ND12-898 | nt |  |  |  |
|  | N-F1008 | nt | Ear | Finland | 1995 |
|  | N-F487 | nt | Ear | Finland | 1995 |
|  | ND21040 | nt | Ear | Detroit, MI | 1995 |
|  | N-A9 | nt | Ear | St Louis, MO | 1985 |
|  | N-F1007 | nt | Ear | Finland | 1995 |
| 34 | b-B6094 | b | CSF | Wycombe, UK | 1985 |
|  | b-B7004 | b | CSF | Holland |  |
|  | b-BEAGAN | b |  |  |  |
|  | b-B7853 | b | CSF | Maryland | 1990 |
|  | b-B8012 | b | Blood | 7 Mile Ja | 1984 |
|  | b-B7017 | b | CSF | Ghana | 1983 |
|  | b-B7118 | b | Blood | Melbourne, A | 1985 |
|  | b-B7651 | b | CSF | Norway | 1980's |
|  | b-B7717 | b |  | Australia | 1989 |
| 35 | N-F430 | nt | Ear | Finland | 1995 |
|  | N-F566 | nt | Ear | Finland | 1995 |
|  | N-F412 | nt | Ear | Finland | 1995 |
|  | N-F413 | nt | Ear | Finland | 1995 |
|  | b-B6107 | b | CSF | Oxford, UK | 1985 |
|  | b-B7020 | b | CSF | Ghana | 1983 |
|  | ND241022 | nt | Res | Rochester, NY | 1995 |
|  | b-B7414 | b |  | Kenya |  |
|  | b-EC129 | b |  |  |  |
|  | N-F285 | nt | Ear | Finland | 1994 |
|  | N-F286 | nt | Ear | Finland | 1994 |
| 36 | a-B6073 | a | Sputum | Newcastle, UK | 1966 |
|  | a-B6083 | a | Sputum | Newcastle, UK |  |
|  | c-B6134 | c | Abcess | Oxford, UK | 1975 |
| 37 | a-ATCC9006 | a |  |  |  |
| 38 | a-B7416 | a | Nasal | Kenya |  |
| 39 | N-A1510 | nt | Ear | Philadelphia, PA | 1980's |
| 40 | ND241028 | nt | CSF | Rochester, NY | 1995 |
|  | ND941 | nt | Blood | Los Angeles, CA | 1994 |
|  | ND111121 | nt | BF | Stanford, CA | 1995 |
|  | ND241025 | nt | CSF | Rochester, NY | 1995 |
|  | N-A16 | nt | Ear | Cleveland, OH | 1986 |
|  | N-A17 | nt | Ear | Cleveland, OH | 1986 |
|  | N-A820A | nt | CSF | St. Louis, MO | 1980's |
|  | N-F658 | nt | Ear | Finland | 1995 |
| 41 | ND17-1188 | nt | Res | Phoenix, AZ | 1995 |
|  | ND231111 | nt | Res | Harford, CT | 1995 |
|  | ND28279 | nt | Res | New York, NY | 1994 |
|  | N-A1396A | nt | CSF | Minneapolis | 1980's |
|  | N-F723 | nt | Ear | Finland | 1995 |
| 42 | ND18178 | nt | BAL | Chapel, NC | 1994 |
| 43 | ND171185 | nt | Res | Phoenix, AZ | 1995 |
|  | ND28-12 | nt | Res | New York, NY | 1994 |
| 44 | N-A24 | nt | Ear | Cleveland, OH | 1982 |
|  | N-A3246A | nt | Ear | Cleveland, OH | 1980's |
|  | N-EC194 | nt | Ear | Regina, Sask. | 1985–87 |
|  | ND111125 | nt | Res | Stanford, CA | 1995 |
| 45 | d-EF33 | d | Sputum | Halifax, NS | 1985–87 |
|  | N-A1878B | nt | Ear | St. Louis, MO | 1980's |
|  | b-EE53 | b | Sputum | Halifax, NS | 1985–87 |
|  | c-B7424 | c |  | Kenya |  |
|  | ND3107 | nt | Res | Evanston, IL | 1994 |
|  | ND3108 | nt | Res | Evanston, IL | 1994 |
|  | ND18177 | nt | Res | Chapel, NC | 1994 |
|  | ND20-144 | nt | Res | Decteur, GA | 1994 |
|  | ND241027 | nt | CSF | Rochester, NY | 1995 |
|  | ND25-209 | nt | CSF | Washington, DC | 1994 |
|  | N-F137 | nt | Ear | Finland | 1994 |
|  | N-EI71 | nt | Sputum | Ste.-Foy, Que. | 1985–87 |
|  | N-A5 | nt | Ear | St. Louis, MO | 1985 |
|  | N-EE165 | nt | Eye | Winnipeg, Man. | 1985–87 |
|  | N-F973 | nt | Ear | Finland | 1995 |
|  | ND1-1078 | nt | Res | Cleveland, OH | 1995 |

TABLE 1-continued

| Lineage | Strain | Sero-type | Infection | Geographic location | Year |
|---|---|---|---|---|---|
|  | ND10-188 | nt | Res | Clackamas, OR | 1994 |
|  | ND18176 | nt | Res | Chapel, NC | 1994 |
| 46 | ND41095 | nt | Res | Rochester, MN | 1994 |
|  | ND8-1175 | nt | Res | St. Louis, MO | 1995 |
| 47 | b-EOT165 | b | CSF | Ottawa, Ont. | 1985–87 |
|  | c-B8032 | c |  |  | 1983 |
|  | b-ELO29 | b | CSF | London, Ont. | 1985–87 |
|  | b-ELO38 | b | CSF | London, Ont. | 1985–87 |
|  | N-F1117 | nt | Ear | Finland | 1995 |
|  | N-F486 | nt | Ear | Finland | 1995 |
|  | ND31032 | nt | Res | Evanston, IL | 1995 |
|  | a-B7205 | a | CSF | Gambia | 1984 |
|  | a-EE163 | a | CSF | Winnipeg, Man. | 1985–87 |
| 48 | ND221153 | nt | Res | Boston, MA | 1995 |
| 49 | ND25-489 | nt | CSF | Washingtion, DC | 1994 |
|  | ND301076 | nt | BF | Syracuse, NY | 1995 |
| 50 | c-EOT36 | c | CSF | Ottawa, Ont. | 1985–87 |
|  | N-A1136B | nt | Blood | St. Louis, MO | 1980's |
|  | c-B1271 | c |  | Chicago, IL | 1968 |
|  | c-B7267 | c | Sputum | Malaysia | 1973 |
|  | N-EOT126 | nt | CSF | Ottawa, Ont. | 1985–87 |
|  | b-ESJ133 | b | CSF | Montreal, Que. | 1985–87 |
|  | c-B1167 | c |  | Massachusetts |  |
| 51 | c-B7270 | c | Sputum | Malaysia | 1975 |
| 52 | ND21-1204 | nt | SA | Mobile, AL | 1995 |
| 53 | ND12-599 | nt |  |  |  |
| 54 | c-B6132 | c | Nasal | Newcastle, UK | 1964 |
|  | c-ATCC9007 | c |  |  |  |
|  | c-B6129 | c |  | Wellcomb Res. Lab. | 1970 |
| 55 | N-A31 | nt | Ear | Cleveland, OH | 1983 |
|  | N-CBCH-2 | nt |  | Boston, MA |  |
|  | a-EC140 | a | Ear | Regina, Sask. | 1985–87 |
|  | N-A1514A | nt | Ear | Philadelphia, PA | 1980's |
|  | ND25-62 | nt | CSF | Washington, DC | 1994 |
|  | ND3-1553 | nt |  |  |  |
|  | N-F176 | nt | Ear | Finland | 1994 |
|  | N-F477 | nt | Ear | Finland | 1995 |
|  | N-F478 | nt | Ear | Finland | 1995 |
|  | ND13-113 | nt | Res | Houston, TX | 1994 |
| 56 | ND2-1037 | nt | SA | Detroit, MI | 1995 |
| 57 | ND6-1453 | nt |  |  |  |
|  | ND6-1490 | nt |  |  |  |
|  | ND3-1552 | nt |  |  |  |
|  | ND41097 | nt | Res | Rochester, MN | 1994 |
|  | ND18175 | nt | Res | Chapel, NC | 1994 |
|  | ND18179 | nt | Res | Chapel, NC | 1994 |
|  | ND21039 | nt | CSF | Detroit, MI | 1995 |
|  | ND23-926 | nt |  |  |  |
|  | N-F1104 | nt | Ear | Finland | 1995 |
|  | N-F1106 | nt | Ear | Finland | 1995 |
|  | N-EA57 | nt | Sputum | Montreal, Que. | 1985–87 |
|  | N-F1061 | nt | Ear | Finland | 1995 |
|  | c-EC117 | c | Tracheal | Regina, Sask. | 1985–87 |
|  | e-EF142 | e | Eye | Halifax, NS | 1985–87 |
|  | N-CBCH-1 | nt |  | Boston, MA |  |
|  | N-CBCH-3 | nt | Nasopharynx | Boston, MA |  |
|  | N-F1232 | nt | Ear | Finland | 1995 |
|  | N-F758 | nt | Ear | Finland | 1995 |
|  | N-F1147 | nt | Ear | Finland | 1995 |
|  | N-F1231 | nt | Ear | Finland | 1995 |
|  | N-F886 | nt | Ear | Finland | 1995 |
|  | ND16-1529 | nt | CSF | Dallas, TX | 1995 |
|  | ND171187 | nt | Res | Phoenix, AZ | 1995 |
|  | ND18-984 | nt |  |  |  |
| 58 | N-EA73 | nt | Ear | Montreal, Que. | 1985–87 |
|  | ND121120 | nt | Ear | Seattle, WA | 1995 |
| 59 | ND28-15 | nt | BF | New York, NY | 1994 |
| 60 | e-B6181 | e | Sputum | Newcastle, UK | 1965 |
| 61 | e-B6168 | e |  | Newcastle, UK | 1964 |
|  | e-B6169 | e | Sputum | Newcastle, UK | 1966 |
|  | e-B7066 | e | Lung asp. | Papua New Guinea |  |
| 62 | ND231113 | nt | Blood | Harford, CT | 1995 |
| 63 | N-F740 | nt | Ear | Finland | 1995 |
| 64 | e-B8031 | e | Throat | Canyon Bay, USA | 1983 |
|  | ND21-1203 | nt | Ear | Mobile, AL | 1995 |
|  | e-B7287 | e | Sputum | Malaysia | 1973 |

TABLE 1-continued

| Lineage | Strain | Sero-type | Infection | Geographic location | Year |
|---|---|---|---|---|---|
| | e-B7423 | e | Nasal | Kenya | |
| | ND221152 | nt | BF | Boston, MA | 1995 |
| | ND241020 | nt | Res | Rochester, NY | 1995 |
| | e-ATCC8142 | e | | | |
| | e-B1018 | e | | Indiana, USA | 1987 |
| | e-B6158 | e | Sputum | Newcastle, UK | 1962 |
| | e-B6229 | e | Sputum | Oxford, UK | 1977 |
| 65 | ND1-1081 | nt | Res | Cleveland, OH | 1995 |
| 66 | ND8-102 | nt | BF | St. Louis, MO | 1994 |
| 67 | ND12-1116 | nt | Ear | Seattle, WA | 1995 |
| 68 | ND41099 | nt | Res | Rochester, MN | 1994 |
| 69 | ND301072 | nt | Ear | Syracuse, NY | 1995 |
| 70 | ND11083 | nt | CSF | Cleveland, OH | 1995 |
| 71 | N-A11 | nt | Ear | Cleveland, OH | 1985 |
| 72 | N-A1396B | nt | CSF | Minneapolis | 1980's |
| 73 | N-A3837B | nt | Ear | Cleveland, OH | 1980's |
| | N-F199 | nt | Ear | Finland | 1994 |
| | ND271006 | nt | Res | Worcester, MA | 1994 |
| | N-F200 | nt | Ear | Finland | 1994 |
| | N-F218 | nt | Ear | Finland | 1994 |
| 74 | ND1-1077 | nt | Res | Cleveland, OH | 1995 |
| 75 | NL-EOT149 | nt | Sputum | Ottawa, Ont. | 1985–87 |
| 76 | ND28-11 | nt | Res | New York, NY | 1994 |
| 77 | ND11085 | nt | Res | Cleveland, OH | 1995 |
| 78 | N-F1181 | nt | Ear | Finland | 1995 |
| | N-F1251 | nt | Ear | Finland | 1995 |
| | ND23134 | nt | Res | Hartford, CT | 1994 |
| | N-F942 | nt | Ear | Finland | 1995 |
| | N-F943 | nt | Ear | Finland | 1995 |
| | N-F1292 | nt | Ear | Finland | 1995 |
| | N-F1306 | nt | Ear | Finland | 1995 |
| | N-F1414 | nt | Ear | Finland | 1995 |
| | N-F1543 | nt | Ear | Finland | 1995 |
| 79 | N-F1180 | nt | Ear | Finland | 1995 |
| | ND18171 | nt | CSF | Chapel, NC | 1994 |
| 80 | f-B7290 | f | Sputum | Malaysia | 1974 |
| | ND231114 | nt | Ear | Hartford, CT | 1995 |
| 81 | f-B6255 | f | Sputum | Newcastle, UK | 1967 |
| | f-B7283 | f | Sputum | Malaysia | 1972 |
| | f-ATCC9833 | f | | | |
| | f-B6237 | f | Nasal | Newcastle, UK | 1963 |
| | N-F553 | nt | Ear | Finland | 1995 |
| | ND18172 | nt | Res | Chapel, NC | 1994 |
| 82 | N-EC105 | nt | Sputum | Regina, Sask. | 1985–87 |
| | f-ELO117 | f | Eye | London, Ont. | 1985–87 |
| | f-EOT203 | f | Eye | Ottawa, Ont. | 1985–87 |
| 83 | N-F161 | nt | Ear | Finland | 1994 |
| | N-F162 | nt | Ear | Finland | 1994 |
| 84 | f-B6252 | f | Nasal | Newcastle, UK | 1966 |
| 85 | N-F167 | nt | Ear | Finland | 1994 |
| | ND31033 | nt | Res | Evanston, IL | 1995 |
| 86 | N-A1511 | nt | Ear | Philadelphia | 1980's |
| | ND10-242 | nt | Res | Clackamas, OR | 1994 |
| 87 | ND271008 | nt | Res | Worcester, MA | 1994 |
| 88 | ND241024 | nt | Res | Rocester, NY | 1995 |
| | ND271001 | nt | Res | Worcester, MA | 1994 |
| | ND23133 | nt | Res | Hartford, CT | 1994 |
| | ND241021 | nt | Res | Rocester, NY | 1995 |
| | b-EOT22 | b | Sputum | Ottawa, Ont. | 1985–87 |
| | N-F1017 | nt | Ear | Finland | 1995 |
| | ND31030 | nt | Res | Evanston, IL | 1995 |
| | N-F599 | nt | Ear | Finland | 1995 |
| | N-F667 | nt | Ear | Finland | 1995 |
| | N-F708 | nt | Ear | Finland | 1995 |
| | ND20-143 | nt | Res | Decteur, GA | 1994 |
| 89 | DK-1 E. COLI | | | | |
| 90 | ATCC27088 AP | | | | |

TABLE 2

List of restriction enzymes (alphabetical order), cutting *H. influenzae* Rd rrnA 5 times or less, with positions of restriction sites indicated.

| Enzyme | Freq | Position(s) |
|---|---|---|
| Aot II | 1 | 1190 |
| ↓ | | |
| G ACGT C | | |
| C TGCA G | | |
| ↑ | | |
| Aco III | 1 | 365 |
| TGCGCA | | |
| ACGCGT | | |
| Acc I | 3 | 1241 1586 5077 |
| ↓ | | |
| GT MK AC | | |
| CA KM TG | | |
| ↑ | | |
| Acc III | 2 | 1297 3757 |
| ↓ | | |
| T CCGG A | | |
| A GGCC T | | |
| ↑ | | |
| Ace II | 1 | 3992 |
| ↓ | | |
| G CTAG C | | |
| C GATC G | | |
| ↑ | | |
| Ace III | 3 | 1074 3788 4825 |
| ↓ | | |
| CAGCTCNNNNNNNN NNNN | | |
| GTCGAGNNNNNNN NNNN | | |
| ↑ | | |
| Acr I | 5 | 1377 2468 3917 4259 5143 |
| CYCGRG | | |
| GRGCYC | | |
| Afo24R I | 1 | 3968 |
| GCCGGC | | |
| CGGCCG | | |
| Aft III | 3 | 679 1223 2644 |
| ↓ | | |
| A CRYG T | | |
| T GYRC A | | |
| ↑ | | |
| Aft IV | 2 | 652 2718 |
| AGTACT | | |
| TCATGA | | |
| Age 1 | 1 | 4007 |
| ↓ | | |
| A CCGG T | | |
| T GGCC A | | |
| ↑ | | |
| Alw I | 3 | 1533 1830 4646 |
| ↓ | | |
| GGATCNNNN N | | |
| CCTAGNNNN N | | |
| ↑ | | |
| AlwN I | 2 | 1046 4492 |
| ↓ | | |
| CAG NNN CTG | | |
| GTC NNN GAC | | |
| ↑ | | |
| Amo I | 1 | 1346 |
| TCGCGA | | |
| AGCGCT | | |
| Aos III | 2 | 522 4304 |
| CCGCGG | | |
| GGCGCC | | |
| Apo I | 2 | 927 2675 |
| ↓ | | |
| G GGCC C | | |
| C CCGG G | | |
| ↑ | | |
| Aqu1 | 5 | 1378 2469 3918 4260 5144 |
| ↓ | | |
| C YCGR G | | |
| G RGCY C | | |

TABLE 2-continued

| Enzyme | Freq | Position(s) |
|---|---|---|
| ↑ | | |
| Ase1 | 1 | 1890 |
| ↓ | | |
| AT TA AT | | |
| TA AT TA | | |
| ↑ | | |
| Asp52 I | 3 | 77 2332 4599 |
| AAGCTT | | |
| TTCGAA | | |
| Asp5h I | 1 | 213 |
| GCATGC | | |
| CGTACG | | |
| Asp 78 I | 1 | 412 |
| AGGCCT | | |
| TCCGGA | | |
| Ate I | 2 | 1406 2952 |
| CCATGG | | |
| GGTACC | | |
| AtuC I | 1 | 11 |
| TGATCA | | |
| ACTAGT | | |
| Avo I | 5 | 1378 2469 3918 4260 5144 |
| ↓ | | |
| C YCGR G | | |
| G RGCY C | | |
| ↑ | | |
| Avr II | 1 | 621 |
| ↓ | | |
| C CTAG G | | |
| G GATC C | | |
| ↑ | | |
| Boe I | 2 | 788 4630 |
| ACNNNNGTAYC | | |
| TGNNNNCATRG | | |
| Boe I | 2 | 814 4656 |
| NNNNNNNNNNNNNNNACNNN | | |
| NNNNNNNNNNNNNNNNTGNNN | | |
| Bol I | 1 | 4245 |
| ↓ | | |
| TGG CCA | | |
| ACC GGT | | |
| ↑ | | |
| Bon I | 3 | 847 4755 5508 |
| ↓ | | |
| G GYRC C | | |
| C CRYG G | | |
| ↑ | | |
| Bon II | 4 | 232 927 1006 2675 |
| ↓ | | |
| G RGCY C | | |
| C YCGR G | | |
| ↑ | | |
| Bovl | 2 | 1794 4024 |
| ↓ | | |
| CAG CTG | | |
| GTC GAC | | |
| ↑ | | |
| Bbf7411 I | 2 | 1296 3756 |
| TCCGGA | | |
| AGGCCT | | |
| Bbr I | 3 | 78 2333 4600 |
| ↓ | | |
| A AGCT T | | |
| T TCGA A | | |
| ↑ | | |
| Bbs 1 | 3 | 1548 3567 5278 |
| ↓ | | |
| GAAGACNN NNNN | | |
| CTTCTGNN NNNN | | |
| ↑ | | |
| Bce83 I | 3 | 3121 3929 5153 |
| CTTGAGNNNNNNNNNNNNNNN | | |
| GAACTCNNNNNNNNNNNNNNN | | |
| Bcg I | 1 | 1072 |
| GCANNNNNNTCGNNNNNNN | | |
| CGTNNNNNNAGCNNNNNNN | | |
| Bcg I | 1 | 1038 |

TABLE 2-continued

| Enzyme | Freq | Position(s) |
|---|---|---|
| ↓ NN NNNNNNNNNNGCANNN NN NNNNNNNNNNCGTNNN ↑ | | |
| Bcl I<br>↓<br>T GATC A<br>A CTAG T<br>↑ | 1 | 12 |
| Bco102 II<br>GAAGAC<br>CTTCTG | 3 | 1540 3559 5270 |
| Bco163 I<br>CTRYAG<br>GAYRTC | 2 | 1621 4338 |
| Bco35 I<br>CTGGAG<br>GACCTC | 2 | 1167 2984 |
| Bcu1<br>↓<br>ACTAGT<br>TGATCA<br>↑ | 2 | 3363 3369 |
| Bfi891<br>↓<br>Y GGCC R<br>R CCGG Y<br>↑ | 3 | 889 4166 4243 |
| Bfm I<br>↓<br>C TRYA G<br>G AYRT C<br>↑ | 2 | 1622 4339 |
| Bgl I<br>↓<br>GCCN NNN NGGC<br>CGGN NNN NCCG<br>↑ | 2 | 3151 5149 |
| Bl149 I<br>GGTCTC<br>CCAGAG | 3 | 4477 4515 5434 |
| Blp I<br>GCTNAGC<br>CGANTCG | 1 | 1790 |
| Bme142 I<br>↓<br>RGC GCY<br>YCG CGR<br>↑ | 2 | 1804 3906 |
| BmeT1<br>TGATCA<br>ACTAGT | 1 | 11 |
| Bp1 I<br>↓<br>GAGNNNNNCTC<br>CTCNNNNNGAG<br>↑ | 4 | 1269 1280 3187 3198 |
| Bpm I<br>CTGGAGNNNNNNNNNNNNNNNN<br>GACCTCNNNNNNNNNNNNNNNN | 2 | 1189 3006 |
| Bpu10 I<br>↓<br>CC TNA GC<br>GG ANT CG<br>↑ | 2 | 1628 3259 |
| Bpu1268 I<br>CCTNNNNNAGG<br>GGANNNNNTCC | 2 | 338 1443 |
| Bso I<br>↓<br>GGTCTCN NNNN<br>CCAGAGN NNNN<br>↑ | 3 | 4484 4522 5429 |
| Bso XI<br>↓<br>ACNNNNCTCC<br>TGNNNNNGAGG | 2 | 2562 3809 |

TABLE 2-continued

| Enzyme | Freq | Position(s) |
|---|---|---|
| ↑<br>Bso0 I<br>↓<br>CG RY CG<br>GC YR GC<br>↑ | 5 | 875 892 4012 4169 4566 |
| BsoA I<br>↓<br>YAC GTR<br>RTG CAY<br>↑ | 4 | 680 1226 2647 2785 |
| BsoG I<br>GWGCWC<br>CWCGWG | 4 | 1001 1558 3123 4540 |
| BsoK I<br>GTTAAC<br>CAATTG | 1 | 2866 |
| BsoM I<br>↓<br>GAATG CN<br>CTTAC GN<br>↑ | 1 | 3518 |
| Bsb I<br>CAACAC<br>GTTGTG | 2 | 1067 2558 |
| BscU I<br>CCANNNNNTGG<br>GGTNNNNNACC | 3 | 1123 1406 4799 |
| Bse59 I<br>GGTNACC<br>CCANTGG | 1 | 1499 |
| BseM1<br>↓<br>GCAATG<br>CGTTAC<br>↑ | 3 | 368 4585 4976 |
| BseR I<br>↓<br>GAGGAGNNNNNNNN NN<br>CTCCTCNNNNNNNN NN<br>↑ | 3 | 2565 4510 4553 |
| Bsg I<br>GTGCAGNNNNNNNNNNNNNN<br>CACGTCNNNNNNNNNNNNNN | 1 | 4208 |
| BshL I<br>GATATC<br>CTATAG | 2 | 2368 2649 |
| BsiHKA I<br>↓<br>G WGCW C<br>C WCGW G<br>↑ | 4 | 1006 1563 3128 4545 |
| BsmBI<br>↓<br>CGTCTCN NNNN<br>GCAGAGN NNNN<br>↑ | 1 | 5355 |
| BsmG I<br>TGTACA<br>ACATGT | 1 | 1386 |
| BsmH I<br>RGCGCY<br>YCGCGR | 2 | 1801 3903 |
| BsoO I<br>CGGCCG<br>GCCGGC | 2 | 888 4165 |
| BsoJI<br>GCCGGC<br>CGGCCG | 1 | 3968 |
| Bsp117 I<br>GRGCYC<br>CYCGRG | 4 | 227 922 1001 2670 |
| Bsp120 I<br>↓<br>G GGCC C<br>C CCGG G<br>↑ | 2 | 923 2671 |

TABLE 2-continued

| Enzyme | Freq | Position(s) |
|---|---|---|
| Bsp19I<br>↓<br>C CATG G<br>G GTAC C<br>↑ | 2 | 1407 2953 |
| Bsp24 I<br>GACNNNNNNTGGNNNNNNN<br>CTGNNNNNNACCNNNNNNN<br>↑ | 3 | 3247 4491 4508 |
| Bsp24 I<br>↓<br>NNNNN NNNNNNNNGACNN<br>NNNNN NNNNNNNNCTGNN<br>↑ | 3 | 3279 4459 4476 |
| Bsp6 II<br>CTGAAG<br>GACTTC | 4 | 1538 3802 3995 4787 |
| Bsp87 I<br>CACGTG<br>GTGCAC | 3 | 677 1223 2644 |
| BspG I<br>CTGGAC<br>GACCTG | 2 | 329 3492 |
| BspH I<br>↓<br>T CATG A<br>A GTAC T<br>↑ | 1 | 1474 |
| BspKT5I<br>CTGAAGNNNNNNNNNNNNNNN<br>GACTTCNNNNNNNNNNNNNNN | 4 | 1560 3824 4017 4809 |
| BspM I<br>↓<br>ACCTGCNNNN NNNN<br>TGGACGNNNN NNNN<br>↑ | 4 | 1524 2950 4230 4619 |
| BsrD I<br>↓<br>GCAATG NN<br>CGTTAC NN<br>↑ | 3 | 376 4593 4970 |
| BsrE I<br>CTCTTC<br>GAGAAG | 3 | 3 998 4992 |
| BsrFI<br>↓<br>R CCGG Y<br>Y GGCC R<br>↑ | 3 | 500 3969 4007 |
| BsrG I<br>↓<br>T GTAC A<br>A CATG T<br>↑ | 1 | 1387 |
| BsrW I<br>GGATC<br>CCTAG | 3 | 1524 1835 4651 |
| BssS I<br>↓<br>C TCGT G<br>G AGCA C<br>↑ | 1 | 1065 |
| Bst1107 I<br>↓<br>GTA TAC<br>CAT ATG<br>↑ | 1 | 1242 |
| Bst29 I<br>CCTNAGG<br>GGANTCC | 2 | 3609 4184 |
| BstE II<br>↓<br>G GTNAC C<br>C CANTG G<br>↑ | 1 | 1500 |
| BstMPI<br>↓ | 1 | 2869 |
| GTT AAC<br>CAA TTG<br>↑ | | |
| BstX I<br>↓<br>CCAN NNNN NTGG<br>GGTN NNNN NACC<br>↑ | 3 | 1131 1414 4807 |
| BstZ2 I<br>↓<br>GACNNNNGTC<br>CTGNNNNCAG<br>↑ | 4 | 1185 1196 5051 5062 |
| Bsu36 I<br>↓<br>CC TNA GG<br>GG ANT CC<br>↑ | 2 | 3611 4186 |
| Cfr10 I<br>↓<br>R CCGG Y<br>Y GGCC R<br>↑ | 3 | 500 3969 4007 |
| Cfr14 I<br>YGGCCR<br>RCCGGY | 3 | 888 4165 4242 |
| Cfr9I | 1 | 1378 |
| ↓<br>C CCGG G<br>G GGCC C<br>↑ | | |
| CfrJ4I | 1 | 1380 |
| ↓<br>CCC GGG<br>GGG CCC<br>↑ | | |
| Chu II<br>GTYRAC<br>CARYTG | 1 | 2866 |
| Dro I<br>↓<br>TTT AAA<br>AAA TTT<br>↑ | 5 | 1924 1965 2028 3344 4824 |
| Drd I<br>↓<br>GACNN NN NNGTC<br>CTGNN NN NNCAG<br>↑ | 2 | 4620 4866 |
| Drd II<br>GAACCA<br>CTTGGT | 4 | 1668 2713 3068 4658 |
| Dso VI<br>GTMKAC<br>CAKMTG | 3 | 1239 1584 5075 |
| Eoe I<br>↓<br>Y GGCC R<br>R CCGG Y<br>↑ | 3 | 889 4166 4243 |
| Eor I<br>↓<br>CTCTTCN NNN<br>GAGAAGN NNN<br>↑ | 2 | 994 4988 |
| EcoI<br>↓<br>G GTNAC C<br>C CANTG G<br>↑ | 1 | 1500 |
| Eci I<br>TCCGCC<br>AGGCGG | 1 | 101 |
| EclA I<br>TACGTA<br>ATGCAT | 1 | 2782 |
| EclE I | 2 | 922 2670 |

TABLE 2-continued

| Enzyme | Freq | Position(s) |
|---|---|---|
| GGGCCC | | |
| CCCGGG | | |
| Ecl137 I | 1 | 1001 |
| GAGCTC | | |
| CTCGAG | | |
| EclHK I | 2 | 1191 5057 |
| ↓ | | |
| GACNN N NNGTC | | |
| CTGNN N NNCAG | | |
| ↑ | | |
| Eco24I | 4 | 232 927 1006 2675 |
| ↓ | | |
| G RGCY C | | |
| C YCGR G | | |
| ↑ | | |
| Eco31I | 3 | 4484 4522 5429 |
| ↓ | | |
| GGTCTCN NNNN | | |
| CCAGAGN NNNN | | |
| ↑ | | |
| Eco50 I | 3 | 846 4754 5507 |
| GGYRCC | | |
| CCRYGG | | |
| Eco52 I | 2 | 889 4166 |
| ↓ | | |
| C GGCC G | | |
| G CCGG C | | |
| ↑ | | |
| Eco57 I | 4 | 1560 3824 4017 4809 |
| CTGAAGNNNNNNNNNNNNNNNN | | |
| GACTTCNNNNNNNNNNNNNNNN | | |
| Eco64I | 3 | 847 4755 5508 |
| ↓ | | |
| G GYRC C | | |
| C CRYG G | | |
| ↑ | | |
| Eco72 I | 3 | 680 1226 2647 |
| ↓ | | |
| CAC GTG | | |
| GTG CAC | | |
| ↑ | | |
| Eco82 I | 2 | 671 2418 |
| GAATTC | | |
| CTTAAG | | |
| Eco88I | 5 | 1378 2469 3918 4260 5144 |
| ↓ | | |
| C YCGR G | | |
| G RGCY C | | |
| ↑ | | |
| EcoD I | 5 | 118 1609 1896 3262 |
| ↓ | | |
| YYANNNNNNNGTCY | | |
| AATNNNNNNNCAGR | | |
| ↑ | | |
| EcoD XXI | 3 | 1370 4242 5459 |
| ↓ | | |
| TCANNNNNNNRTTC | | |
| AGTNNNNNNNYAAG | | |
| ↑ | | |
| EcoDR2 | 1 | 3011 |
| ↓ | | |
| TCANNNNNNGTCG | | |
| AGTNNNNNNCAGC | | |
| ↑ | | |
| EcoE I | 1 | 205 |
| ↓ | | |
| GAGNNNNNNNATGC | | |
| CTCNNNNNNNTACG | | |
| ↑ | | |
| Eco1CR I | 1 | 1004 |
| ↓ | | |
| GAG CTC | | |
| CTC GAG | | |
| ↑ | | |
| EcoN I | 2 | 343 1448 |
| ↓ | | |
| CCTNN N NNAGG | | |

| Enzyme | Freq | Position(s) |
|---|---|---|
| GGANN N NNTCC | | |
| ↑ | | |
| EcoO109 I | 4 | 923 2671 3263 4796 |
| ↓ | | |
| RG GNC CY | | |
| YC CNG GR | | |
| ↑ | | |
| EcoP15 I | 2 | 380 547 |
| CAGCAGNNNNNNNNNNNNNNNN | | |
| GTCGTCNNNNNNNNNNNNNNNN | | |
| EcoR I | 2 | 672 2419 |
| ↓ | | |
| G AATT C | | |
| C TTAA G | | |
| ↑ | | |
| EcoR V | 2 | 2371 2652 |
| ↓ | | |
| GAT ATC | | |
| CTA TAG | | |
| ↑ | | |
| EcoR124 I | 2 | 1326 4272 |
| ↓ | | |
| GAANNNNNNRTCG | | |
| CTTNNNNNNYAGC | | |
| ↑ | | |
| EcoR124 II | 4 | 1350 3623 4135 4195 |
| ↓ | | |
| GAANNNNNNNRTCG | | |
| CTTNNNNNNNYAGC | | |
| ↑ | | |
| EcoR02 | 2 | 3542 5286 |
| ↓ | | |
| GAANNNNNNRTTC | | |
| CTTNNNNNNYAAG | | |
| ↑ | | |
| EcoVIII | 3 | 78 2333 4600 |
| ↓ | | |
| A AGCT T | | |
| T TCGA A | | |
| ↑ | | |
| Ecaprr I | 1 | 644 |
| ↓ | | |
| CCANNNNNNNNRTGC | | |
| GGTNNNNNNNNYACG | | |
| ↑ | | |
| Esp16 I | 1 | 5360 |
| CGTCTC | | |
| GCAGAG | | |
| Esp3 I | 1 | 5355 |
| ↓ | | |
| CGTCTCN NNNN | | |
| GCAGAGN NNNN | | |
| ↑ | | |
| FbII | 3 | 1241 1586 5077 |
| ↓ | | |
| GT NK AC | | |
| CA KM TG | | |
| ↑ | | |
| Fsp I | 1 | 368 |
| ↓ | | |
| TGC GCA | | |
| ACG CGT | | |
| ↑ | | |
| Fsu I | 3 | 323 1128 4484 |
| GACNNNGTC | | |
| CTGNNNCAG | | |
| Gdi II | 4 | 893 894 4170 4171 |
| ↓ | | |
| CGGCC R | | |
| GCCGG Y | | |
| ↑ | | |
| Gsp I | 2 | 1791 4021 |
| CAGCTG | | |
| GTCGAC | | |
| Hoe I | 3 | 415 3047 4245 |
| ↓ | | |
| WGG CCW | | |

TABLE 2-continued

| Enzyme | Freq | Position(s) |
|---|---|---|
| WCC GGW ↑ | | |
| Hoe II ↓ | 2 | 1806 3908 |
| R GCGC Y | | |
| Y CGCG R ↑ | | |
| HoII ↓ | 2 | 672 2419 |
| G AATT C | | |
| C TTAA G ↑ | | |
| Hgo I ↓ | 5 | 395 759 4411 4944 4976 |
| GACGCNNNNN NNNNN | | |
| CTGCGNNNNN NNNNN ↑ | | |
| HglCI ↓ | 3 | 847 4755 5508 |
| G GYRC C | | |
| C CRYG G ↑ | | |
| HgiE II | 2 | 3110 3871 |
| ACCNNNNNNNGGT | | |
| TGGNNNNNNNCCA | | |
| HinB³¹ I | 2 | 1185 4401 |
| GRCGYC | | |
| CYGCRG | | |
| HinJCI ↓ | 1 | 2869 |
| GTY RAC | | |
| CAR YTG ↑ | | |
| Hinc II ↓ | 1 | 2869 |
| GTY RAC | | |
| CAR-YTG ↑ | | |
| Hind III ↓ | 3 | 78 2333 4600 |
| A AGCT³¹ T⁻ | | |
| T TCGA A ↑ | | |
| Hpo I ↓ | 1 | 2869 |
| GTT AAC | | |
| CAA TTG ↑ | | |
| Hsp92 I ↓ | 2 | 1187 4403 |
| GR CG YC | | |
| CY GC RG ↑ | | |
| Lsp1270 I | 3 | 50 213 942 |
| RCATGY | | |
| YGTACR | | |
| M. SmaDam | 2 | 2368 2649 |
| GATATC | | |
| CTATAG | | |
| Mlu1106 I | 2 | 3261 4794 |
| RGGWCCY | | |
| YCCWGGR | | |
| Mlu113 I | 2 | 524 4306 |
| ↓ | | |
| CC GC GG | | |
| GG CG CC ↑ | | |
| MscI ↓ | 1 | 4245 |
| TGG CCA | | |
| ACC GGT ↑ | | |
| Msl I ↓ | 4 | 1412 4069 4239 4761 |
| CAYNN NNRTG | | |
| GTRNN NNYAC ↑ | | |

TABLE 2-continued

| Enzyme | Freq | Position(s) |
|---|---|---|
| Nsp20 I ↓ | 2 | 4242 4248 |
| TGGCCA | | |
| ACCGGT ↑ | | |
| NspA1 I ↓ | 5 | 525 1794 1829 4024 4307 |
| CMG CKG | | |
| GKC GMC ↑ | | |
| Noe I ↓ | 1 | 3971 |
| GCC GGC | | |
| CGG CCG ↑ | | |
| Nco I ↓ | 2 | 1407 2953 |
| C CATG G | | |
| G GTAC C ↑ | | |
| NgoM I ↓ | 1 | 3969 |
| G CCGG C | | |
| C GGCC G ↑ | | |
| Nhe 1 ↓ | 1 | 3988 |
| G CTAG C | | |
| C GATC G ↑ | | |
| Nii387/7 I ↓ | 5 | 1382 2473 3922 4264 5148 |
| C YCGR G | | |
| G RGCY C ↑ | | |
| Nru I ↓ | 1 | 1349 |
| TCG CGA | | |
| AGC GCT ↑ | | |
| Nsp 1 ↓ | 3 | 55 218 947 |
| R CATG Y | | |
| Y GTAC R ↑ | | |
| Pfl1108 I | 2 | 3173 5080 |
| TCGTAG | | |
| AGCATC | | |
| PinA1 ↓ | 1 | 4007 |
| A CCGG T | | |
| T GGCC A ↑ | | |
| Ppe1 ↓ | 2 | 927 2675 |
| G GGCC C | | |
| C CCGG G ↑ | | |
| Ppu1253 1 | 1 | 1185 |
| GACGTC | | |
| CTGCAG | | |
| Ppu6 1 | 4 | 677 1223 2644 2782 |
| YACGTR | | |
| RTGCAY | | |
| PpuM I ↓ | 2 | 3263 4796 |
| RG GWC CY | | |
| YC CWG GR ↑ | | |
| PshA I ↓ | 1 | 4406 |
| GACNN NNGTC | | |
| CTGNN NNCAG ↑ | | |
| Psp1406 I ↓ | 2 | 3582 4445 |
| AA CG TT | | |

TABLE 2-continued

| Enzyme | Freq | Position(s) |
|---|---|---|
| TT GC AA ↑ PspAI ↓ C CCGG G G GGCC C ↑ | 1 | 1378 |
| Pss I ↓ RG GNC CY YC CNG GR ↑ | 4 | 926 2674 3266 4799 |
| Pvu II ↓ CAG CTG GTC GAC ↑ | 2 | 1794 4024 |
| Rhc I TCATGA AGTACT | 1 | 1473 |
| RleA I ↓ CCCACANNNNNNNNN NNN GGGTGTNNNNNNNNN NNN ↑ | 2 | 3670 5472 |
| Soc I ↓ G AGCT C C TCGA G ↑ | 1 | 1006 |
| Soc II ↓ CC GC GG GG CG CC ↑ | 2 | 526 4308 |
| Sop I ↓ GCTCTTCN NNN ↑ | 1 | 994 |
| SouLPI ↓ GCC GGC CGG CCG ↑ | 1 | 3971 |
| Sco I ↓ AGT ACT TCA TGA ↑ | 2 | 655 2721 |
| Sfc I ↓ C TRYA G G AYRT C ↑ | 2 | 1622 4339 |
| SgrA I ↓ CR CCGG YG GY GGCC RC ↑ | 1 | 3969 |
| Smo I ▽ CCC GGG GGG CCC | 1 | 1380 |
| SmlI ↓ C TYRA G G ARYT C ↑ | 3 | 3100 3908 5168 |
| Sno I GTATAC CATATG | 1 | 1239 |
| SnoB I ↓ TAC GTA ATG CAT ↑ | 1 | 2785 |
| Spe I ↓ A CTAG T T GATC A ↑ | 1 | 3364 |
| Sph I ↓ G CATG C C GTAC G ↑ | 1 | 218 |
| SsoI ↓ G AATT C C TTAA G ↑ | 2 | 672 2419 |
| Ssp I ↓ AAT ATT TTA TAA ↑ | 3 | 363 1928 3654 |
| SstI ↓ G AGCT C C TCGA G ↑ | 1 | 1006 |
| Stu I ↓ AGG CCT TCC GGA ↑ | 1 | 415 |
| StySJ ↓ GAGNNNNNNGTRC CTCNNNNNNCAYG | 1 | 1412 |
| StySKI ↓ CGATNNNNNNNGTTA GCTANNNNNNCAAT | 1 | 873 |
| StySP I ↓ AACNNNNNNGTRC TTGNNNNNNCAYG ↑ | 1 | 2455 |
| Syn II GAANNNNTTC CTTNNNNAAG | 3 | 410 1368 3430 |
| Toq II ↓ GACCGANNNNNNNNN NN CTGGCTNNNNNNNNN NN ↑ | 3 | 2720 3007 4856 |
| Toq II ↓ CACCCANNNNNNNNN NN GTGGGTNNNNNNNNN NN ↑ | 1 | 5088 |
| TthIII I ↓ GACN N NGTC CTGN N NCAG ↑ | 3 | 327 1132 4488 |
| TthIII II ↓ CAARCANNNNNNNNN NN GTTYGTNNNNNNNNN NN ↑ | 3 | 109 2647 4740 |
| Ubo1220 I CCCGGG GGGCCC | I | 1377 |
| Ubo1221 1 ↓ GCTNAGC CGANTCG ↑ | 2 | 1788 1795 |
| Ubo1303 I | 5 | 871 888 4008 4165 4562 |

TABLE 2-continued

List of restriction enzymes (alphabetical order), cutting *H. influenzae* Rd rrnB 5 times or less, with positions of restriction sites indicated.

| Enzyme | Freq | Position(s) |
|---|---|---|
| CGRYCG |  |  |
| GCYRGC |  |  |
| Ubo1326 I | 4 | 921 2669 3261 4794 |
| RGGNCCY |  |  |
| YCCNGGR |  |  |
| Ubo1382 I | 1 | 3511 |
| GAATGC |  |  |
| CTTACG |  |  |
| Von 91 I | 1 | 2612 |
| ↓ |  |  |
| CCAN NNN NTGG |  |  |
| GGTN NNN NACC |  |  |
| ↑ |  |  |
| Vsp I | 1 | 1890 |
| ↓ |  |  |
| AT TA AT |  |  |
| TA AT TA |  |  |
| ↑ |  |  |
| Xcm I | 1 | 1164 |
| ↓ |  |  |
| CCANNNN N NNNNTGG |  |  |
| GGTNNNN N NNNNACC |  |  |
| ↑ |  |  |
| Xmo I | 1 | 1378 |
| ↓ |  |  |
| C CCGG G |  |  |
| G GGCC C |  |  |
| ↑ |  |  |
| XmoIII | 2 | 889 4166 |
| ↓ |  |  |
| C GGCC G |  |  |
| G CCGG C |  |  |
| ↑ |  |  |
| Xmn I | 3 | 415 1373 3435 |
| ↓ |  |  |
| GAANN NNTTC |  |  |
| CTTNN NNAAG |  |  |
| ↑ |  |  |
| Aot II | 1 | 1189 |
| ↓ |  |  |
| G ACGT C |  |  |
| C TGCA G |  |  |
| ↑ |  |  |
| Aco I | 1 | 1721 |
| TTCGAA |  |  |
| AAGCTT |  |  |
| Aco III | 1 | 364 |
| TGCGCA |  |  |
| ACGCGT |  |  |
| Acc I | 3 | 1240 1585 4831 |
| ↓ |  |  |
| CT MK AC |  |  |
| CA KM TG |  |  |
| ↑ |  |  |
| Acc III | 2 | 1296 3511 |
| ↓ |  |  |
| T CCGG A |  |  |
| A GGCC T |  |  |
| ↑ |  |  |
| Ace II | 1 | 3746 |
| ↓ |  |  |
| G CTAG C |  |  |
| C GATC G |  |  |
| ↑ |  |  |
| Ace III | 3 | 1073 3542 4579 |
| ↓ |  |  |
| CAGCTCNNNNNNN NNNN |  |  |
| GTCGAGNNNNNNN NNNN |  |  |
| ↑ |  |  |
| Acr I | 5 | 1376 2222 3671 4013 4897 |
| CYCGRG |  |  |
| GRGCYC |  |  |
| AcsI | 5 | 671 2173 3185 3951 4115 |
| ↓ |  |  |
| R AATT Y |  |  |
| Y TTAA R |  |  |
| ↑ |  |  |
| Afa24R I | 1 | 3722 |
| GCCGGC |  |  |
| CGGCCG |  |  |
| Afl III | 3 | 678 1222 2398 |
| ↓ |  |  |
| A CRYG T |  |  |
| T GYRC A |  |  |
| ↑ |  |  |
| Afl IV | 2 | 651 2472 |
| AGTACT |  |  |
| TCATGA |  |  |
| Age 1 | 1 | 3761 |
| ↓ |  |  |
| A CCGG T |  |  |
| T GGCC A |  |  |
| ↑ |  |  |
| Alw I | 2 | 1532 4400 |
| ↓ |  |  |
| GGATCNNNN N |  |  |
| CCTAGNNNN N |  |  |
| ↑ |  |  |
| AlwN I | 2 | 1045 4246 |
| ↓ |  |  |
| CAG NNN CTG |  |  |
| GTC NNN GAC |  |  |
| Ama I | 1 | 1345 |
| TCGCGA |  |  |
| AGCGCT |  |  |
| Aos III | 2 | 521 4058 |
| CCGCGG |  |  |
| GGCGCC |  |  |
| Apo I | 2 | 926 2429 |
| ↓ |  |  |
| G GGCC C |  |  |
| C CCGG G |  |  |
| ↑ |  |  |
| Apo I | 5 | 671 2173 3185 3951 4115 |
| ↓ |  |  |
| R AATT Y |  |  |
| Y TTAA R |  |  |
| ↑ |  |  |
| AquI | 5 | 1377 2223 3672 4014 4898 |
| ↓ |  |  |
| C YCGR G |  |  |
| G RGCY C |  |  |
| ↑ |  |  |
| Asp52 I | 3 | 76 2086 4353 |
| AAGCTT |  |  |
| TTCGAA |  |  |
| Asp5H I | 1 | 212 |
| GCATGC |  |  |
| CGTACG |  |  |
| Asp78 I | 2 | 411 1683 |
| AGGCCT |  |  |
| TCCGGA |  |  |
| Ate I | 2 | 1405 2706 |
| CCATGG |  |  |
| GGTACC |  |  |
| AtuC I | 1 | 10 |
| TGATCA |  |  |
| ACTAGT |  |  |
| Ava I | 5 | 1377 2223 3672 4014 4898 |
| ↓ |  |  |
| C YCGR G |  |  |
| G RGCY C |  |  |
| ↑ |  |  |
| Avr II | 2 | 620 1687 |
| ↓ |  |  |
| C CTAG G |  |  |
| G GATC C |  |  |
| ↑ |  |  |

TABLE 2-continued

| Enzyme | Freq | Position(s) |
|---|---|---|
| Boe I<br>ACNNNNGTAYC<br>TGNNNNCATRG | 2 | 787 4384 |
| Boe I<br>NNNNNNNNNNNNNNNACNNN<br>NNNNNNNNNNNNNNNNTGNNN | 2 | 813 4410 |
| Bol I<br>↓<br>TGG CCA<br>ACC GGT<br>↑ | 1 | 3999 |
| Bon 1<br>↓<br>G GYRC C<br>C CRYG G<br>↑ | 3 | 846 4509 5262 |
| Bon II<br>↓<br>G RGCY C<br>C YCGR G<br>↑ | 4 | 231 926 1005 2429 |
| Bov1<br>↓<br>CAG CTG<br>GTC GAC<br>↑ | 1 | 3778 |
| Bbf7411 I<br>TCCGGA<br>AGGCCT | 2 | 1295 3510 |
| Bbr I<br>↓<br>A AGCT T<br>T TCGA A<br>↑ | 3 | 77 2087 4354 |
| Bbs I<br>↓<br>GAAGACNN NNNN<br>CTTCTGNN NNNN<br>↑ | 3 | 1547 3321 5032 |
| Bco I<br>GCGC<br>CGCG | 5 | 365 1100 3134 3658 3720 |
| Bce83 I<br>CTTGAGNNNNNNNNNNNNNNN<br>GAACTCNNNNNNNNNNNNNNN | 3 | 2875 3683 4907 |
| Bcg I<br>GCANNNNNNTCGNNNNNNNNN<br>CGTNNNNNNAGCNNNNNNNNN | 1 | 1071 |
| Bcg I<br>↓<br>NN NNNNNNNNNGCANNN<br>NN NNNNNNNNNCGTNNN<br>↑ | 1 | 1037 |
| Bcl I<br>↓<br>T GATC A<br>A CTAG T<br>↑ | 1 | 11 |
| Bco102 II<br>GAAGAC<br>CTTCTG | 3 | 1539 3313 5024 |
| Bco163 I<br>CTRYAG<br>GAYRTC | 1 | 4092 |
| Bco35 I<br>CTGGAG<br>GACCTC | 2 | 1166 2738 |
| Bcu1<br>↓<br>ACTAGT<br>TGATCA<br>↑ | 2 | 3117 3123 |
| Bfi891<br>↓<br>Y GGCC R<br>R CCGG Y<br>↑ | 3 | 888 3920 3997 |
| Bfm I<br>↓<br>C TRYA G<br>G AYRT C<br>↑ | 1 | 4093 |
| Bgl I<br>↓<br>GCCN NNN NGGC<br>CGGN NNN NCCG<br>↑ | 2 | 2905 4903 |
| Bgl I<br>↓<br>GCCN NNN NGGC<br>CGGN NNN NCCG<br>↑ | 2 | 2905 4903 |
| Bl149 I<br>GGTCTC<br>CCAGAG | 3 | 4231 4269 5188 |
| Bme142 I<br>↓<br>RGC GCY<br>YCG CGR<br>↑ | 2 | 3660 |
| BmeTI<br>TGATCA<br>ACTAGT | 1 | 10 |
| Bpl I<br>↓<br>GAGNNNNNCTC<br>CTCNNNNNGAG<br>↑ | 4 | 1268 129 2941 2952 |
| Bpm I<br>CTGGAGNNNNNNNNNNNNNNNN<br>GACCTCNNNNNNNNNNNNNNNN | 2 | 1188 2760 |
| Bpu10 I<br>↓<br>CC TNA GC<br>GG ANT CG<br>↑ | 1 | 3013 |
| Bpu1268 I<br>CCTNNNNNAGG<br>GGANNNNNTCC | 2 | 337 1442 |
| Bso I<br>↓<br>GGTCTCN NNNN<br>CCAGAGN NNNN<br>↑ | 3 | 4238 4276 5183 |
| Bso XI<br>↓<br>ACNNNNNCTCC<br>TGNNNNNGAGG<br>↑ | 2 | 2316 3563 |
| BsoO I<br>↓<br>CG RY CG<br>GC YR GC<br>↑ | 5 | 874 891 3766 3923 4320 |
| BsoA 1<br>↓<br>YAC GTR<br>RTG CAY<br>↑ | 4 | 679 1225 2401 2539 |
| BsoG I<br>GWGCWC<br>CWCGWG | 4 | 1000 1557 4294 |
| BsoK I<br>GTTAAC<br>CAATTG | 1 | 2620 |
| BsoM I<br>↓<br>GAATG CN<br>CTTAC GN<br>↑ | 1 | 3272 |
| Bsb I<br>CAACAC<br>GTTTGYG | 2 | 1066 2312 |
| BscJ I<br>CCANNNNNNTGG | 3 | 1122 1405 4553 |

TABLE 2-continued

| Enzyme | Freq | Position(s) |
|---|---|---|
| GGTNNNNNACC | | |
| Bse59 I | 2 | 1498 1710 |
| GGTNACC | | |
| CCANTGG | | |
| BseMI | 3 | 367 4339 4730 |
| ↓ | | |
|  GCAATG | | |
|  CGTTAC | | |
| ↑ | | |
| BseR I | 3 | 2319 4264 4307 |
| ↓ | | |
| GACGAGNNNNNNNN NN | | |
| CTCCTCNNNNNNNN NN | | |
|               ↑ | | |
| Bsg I | 1 | 3962 |
| GTGCAGNNNNNNNNNNNNNNNN | | |
| CACGTCNNNNNNNNNNNNNNNN | | |
| BshL I | 2 | 2122 2403 |
| GATATC | | |
| CTATAG | | |
| BsiHKA I | 4 | 1005 1562 2882 4299 |
|     ↓ | | |
| G WGCW C | | |
| C WCGW G | | |
|     ↑ | | |
| BsmBI | 1 | 5109 |
| ↓ | | |
| CGTCTCN NNNN | | |
| GCAGAGN NNNN | | |
|           ↑ | | |
| BsmG I | 1 | 1385 |
| TGTACA | | |
| ACATGT | | |
| BsmH I | 1 | 3657 |
| RGCGCY | | |
| YCGCGR | | |
| BsoD I | 2 | 887 3919 |
| CGGCCG | | |
| GCCGGC | | |
| Bsp117 I | 4 | 226 921 1000 2424 |
| GRGCYC | | |
| CYCGRG | | |
| Bsp120 I | 2 | 922 2425 |
| ↓ | | |
| G GGCC C | | |
| C CCGG G | | |
|      ↑ | | |
| Bsp19I | 2 | 1406 2707 |
| ↓ | | |
| C CATG G | | |
| G GTAC C | | |
|     ↑ | | |
| Bsp24 I | 3 | 3001 4245 4262 |
| CACNNNNNNTGNNNNNNN | | |
| CTGNNNNNACCNNNNNNN | | |
| Bsp24 I | 3 | 3033 4213 4230 |
| ↓ | | |
|   NNNNN NNNNNNNNGACNN | | |
|   NNNNN NNNNNNNNCTGNN | | |
| ↑ | | |
| Bsp6 II | 4 | 1537 3556 3749 4541 |
| CTGAAG | | |
| GACTTC | | |
| Bsp87 I | 3 | 676 1222 2398 |
| CACGTG | | |
| GTGCAC | | |
| BspG I | 2 | 328 3246 |
| CTGGAC | | |
| GACCTG | | |
| BspH I | 1 | 1473 |
| ↓ | | |
| T CATG A | | |
| A GTAC T | | |
|     ↑ | | |
| BspKT5 I | 4 | 1559 3578 3771 4563 |
| CTGAAGNNNNNNNNNNNNNN | | |
| GACTTCNNNNNNNNNNNNNN | | |
| BspLU11 II | 2 | 1678 1684 |
| TCTAGA | | |
| AGATCT | | |
| BspM I | 4 | 1523 2704 3984 4373 |
| ↓ | | |
| ACCTGCNNNN NNNN | | |
| TGGACGNNNN NNNN | | |
|                ↑ | | |
| BsrD I | 3 | 375 4347 4724 |
| ↓ | | |
| GCAATG NN | | |
| CGTTAC NN | | |
|      ↑ | | |
| BsrE I | 3 | 2 997 4746 |
| CTCTTC | | |
| GAGAAG | | |
| BsrFI | 3 | 499 3723 3761 |
| ↓ | | |
| R CCGG Y | | |
| Y GGCC R | | |
|     ↑ | | |
| BsrG I | 1 | 1386 |
| ↓ | | |
| T GTAC A | | |
| A CATG T | | |
|     ↑ | | |
| BsrW I | 2 | 1523 4405 |
| GGATC | | |
| CCTAG | | |
| BssS I | 1 | 1064 |
| ↓ | | |
| C TCGT G | | |
| G AGCA C | | |
|     ↑ | | |
| Bst1107 I | 1 | 1241 |
| ↓ | | |
| GTA TAC | | |
| CAT ATG | | |
|    ↑ | | |
| Bst29 I | 2 | 3363 3938 |
| CCTNAGG | | |
| GGANTCC | | |
| BstE II | 2 | 1499 1711 |
| ↓ | | |
| G GTNAC C | | |
| C CANTG G | | |
|      ↑ | | |
| BstHPI | 1 | 2623 |
| ↓ | | |
| GTT AAC | | |
| CAA TTG | | |
|    ↑ | | |
| BstX I | 3 | 1130 1413 4561 |
| ↓ | | |
| CCAN NNNN NTGG | | |
| GGTN NNNN NACC | | |
|     ↑ | | |
| BstZ2 I | 4 | 1184 1195 4805 4816 |
| GACNNNNNGTC | | |
| CTGNNNNNCAG | | |
| Bsu36 I | 2 | 3365 3940 |
| ↓ | | |
| CC TNA GG | | |
| GG ANT CC | | |
|     ↑ | | |
| CfoI | 5 | 368 1103 3137 3723 |
| ↓ | | |
| G CG C | | |
| C GC G | | |
|    ↑ | | |
| Cfr10 I | 3 | 499 3723 3761 |
| ↓ | | |
| R CCGG Y | | |
| Y GGCC R | | |
|     ↑ | | |

TABLE 2-continued

| Enzyme | Freq | Position(s) |
|---|---|---|
| Cfr14 I<br>YGGCCR<br>RCCGGY | 3 | 887 3919 3996 |
| Cfr91<br>↓<br>C CCGG G<br>G GGCC C<br>↑ | 1 | 1377 |
| CfrJ41<br>↓<br>CCC GGG<br>GGG CCC<br>↑ | 1 | 1379 |
| Chu II<br>GTYRAC<br>CARYTG | 1 | 2620 |
| Csp45 I<br>↓<br>TT CG AA<br>AA GC TT<br>↑ | 1 | 1723 |
| Dro I<br>↓<br>TTT AAA<br>AAA TTT<br>↑ | 3 | 1782 3098 4578 |
| Brd I<br>↓<br>GACNN NN NNGTC<br>CTGNN NN NNCAG<br>↑ | 2 | 4374 4620 |
| Drd II<br>GAACCA<br>CTTGGT | 3 | 2467 3822 4412 |
| Dso VI<br>GTMKAC<br>CAKMTG | 3 | 1238 1583 4829 |
| Eoe I<br>V<br>Y GGCC R<br>R CCGG Y<br>↑ | 3 | 888 3920 3997 |
| Eor I<br>↓<br>CTCTTCN NNN<br>GAGAAGN NNN<br>↑ | 2 | 993 4742 |
| EcoI<br>↓<br>G GTNAC C<br>C CANTG G<br>↑ | 2 | 1499 1711 |
| Eci I<br>TCCGCC<br>AGGCGG | 1 | 100 |
| EciA I<br>TACGTA<br>ATGCAT | 1 | 2536 |
| EclE I<br>GGGCCC<br>CCCGGG | 2 | 921 2424 |
| Ecl137 I<br>GAGCTC<br>CTCGAG | 1 | 1000 |
| EclHK I<br>↓<br>GACNN N NNGTC<br>CTGNN N NNCAG<br>↑ | 2 | 1190 4811 |
| Eco24I<br>↓<br>G RGCY C<br>C YCGR G<br>↑ | 4 | 231 926 1005 2429 |
| Eco31I<br>↓<br>GGTCTCN NNNN | 3 | 4238 4276 5183 |

| Enzyme | Freq | Position(s) |
|---|---|---|
| CCAGAGN NNNN<br>↑ | | |
| Eco50 I<br>GGYRCC<br>CCRYGG | 3 | 845 4508 5261 |
| Eco52 I<br>↓<br>C GGCC G<br>G CCGG C<br>↑ | 2 | 888 3920 |
| Eco57 I<br>CTGAAGNNNNNNNNNNNNNN<br>GACTTCNNNNNNNNNNNNNN | 4 | 1559 3578 3771 4563 |
| Eco64I<br>↓<br>G GYRC C<br>C CRYG G<br>↑ | 3 | 846 4509 5262 |
| Eco72 I<br>↓<br>CAC GTG<br>GTG CAC<br>↑ | 3 | 679 1225 2401 |
| Eco82 I<br>GAATTC<br>CTTAAG | 2 | 670 2172 |
| Eco88I<br>↓<br>C YCGR G<br>G RGCY C<br>↑ | 4 | 1377 2223 3672 4014 4898 |
| EcoD I<br>↓<br>TTANNNNNNNGTCY<br>AATNNNNNNNCAGR<br>↑ | 3 | 117 1757 3018 |
| EcoD XXI<br>↓<br>TCANNNNNNNRTTC<br>AGTNNNNNNNYAAG<br>↑ | 3 | 1369 3996 5213 |
| EcoDR2<br>TCANNNNNGTCG<br>AGTNNNNNCAGC<br>↑ | 1 | 2765 |
| EcoE I<br>↓<br>GAGNNNNNNNATGC<br>CTCNNNNNNNTACG<br>↑ | 1 | 204 |
| EcoICR I<br>↓<br>GAG CTC<br>CTC GAG<br>↑ | 1 | 1003 |
| EcoN I<br>↓<br>CCTNN N NNAGG<br>GGANN N NNTCC<br>↑ | 2 | 342 1447 |
| Eco0109 I<br>V<br>RG GNC CY<br>YC CNG GR<br>↑ | 4 | 922 2425 3017 4550 |
| EcoP15 I<br>CAGCAGNNNNNNNNNNNN<br>GTCGTCNNNNNNNNNNNN | 2 | 379 546 |
| EcoR I<br>↓<br>G AATT C<br>C TTAA G<br>↑ | 2 | 671 2173 |
| Eco V<br>↓<br>GAT ATC | 2 | 2125 2406 |

TABLE 2-continued

| Enzyme | Freq | Position(s) |
|---|---|---|
| CTA TAG ↑ | | |
| EcoR124 I ↓ | 2 | 1325 4026 |
| GAANNNNNNRTCG<br>CTTNNNNNNYAGC ↑ | | |
| EcoR124 II ↓ | 4 | 1349 3377 3889 3949 |
| GAANNNNNNNRTCG<br>CTTNNNNNNNYAGC ↑ | | |
| EcoR02 ↓ | 2 | 3296 5040 |
| GAANNNNNNRTTC<br>CTTNNNNNNYAAG ↑ | | |
| EcoVIII ↓ | 3 | 77 2087 4354 |
| A AGCT T<br>T TCGA A ↑ | | |
| Ecoprr I ↓ | 1 | 643 |
| CCANNNNNNNRTGC<br>GGTNNNNNNNYACG ↑ | | |
| Esp15 I<br>CGTCTC<br>GCAGAG | 1 | 5114 |
| Exp3 I ↓ | 1 | 5109 |
| CGTCTCN NNNN<br>GCAGAGN NNNN ↑ | | |
| FbII ↓ | 3 | 1240 1585 4831 |
| GT MK AC<br>CA KM TG ↑ | | |
| Fsp I ↓ | 1 | 367 |
| TGC GCA<br>ACG CGT ↑ | | |
| Fsu I<br>GACNNNGTC<br>CTGNNNCAG | 3 | 322 1127 4238 |
| Gdi II ↓ | 4 | 892 893 3924 3925 |
| CGGCC R<br>GCCGG Y ↑ | | |
| Gsp I<br>CAGCTG<br>GTCGAC | 1 | 3775 |
| Hoe I ↓ | 4 | 414 1886 2801 3999 |
| WGG CCW<br>WCC GGW | | |
| Hoe II ↓ | 1 | 3862 |
| R GCGC Y<br>Y CGCG R ↑ | | |
| HoII ↓ | 2 | 671 2173 |
| G AATT C<br>C TTAA G ↑ | | |
| HgiCI ↓ | 3 | 846 4509 5262 |
| G GYRC C<br>C CRYG G ↑ | | |
| HgiE II<br>ACCNNNNNNGGT | 2 | 2864 3625 |

| Enzyme | Freq | Position(s) |
|---|---|---|
| TGGNNNNNNCCA | | |
| Hho I ↓ | 5 | 368 1103 3137 3661 3723 |
| G CG C<br>C GC G ↑ | | |
| HinB I<br>GRCGYC<br>CYGCRG | 3 | 1184 1737 4155 |
| HinJCI ↓ | 1 | 2623 |
| GTY RAC<br>CAR YTG ↑ | | |
| HinPI I ↓ | 5 | 366 1101 3135 3659 3721 |
| G CG C<br>C GC G ↑ | | |
| Hinc II ↓ | 1 | 2623 |
| GTY RAC<br>CAR YTG ↑ | | |
| Hind III ↓ | 3 | 77 2087 4354 |
| A AGCT T<br>T TCGA A ↑ | | |
| Hpo I ↓ | 1 | 2623 |
| GTT AAC<br>CAA TTG ↑ | | |
| Hsp92 I ↓ | 3 | 1186 1739 4157 |
| GR CG YC<br>CY GC RG ↑ | | |
| Lsp1270 I<br>RCATGY<br>YGTACR | 3 | 49 212 941 |
| M. SmoDom<br>GATATC<br>CTATAG | 2 | 2122 2403 |
| Mlu1106 I<br>RGGWCCY<br>YCCWGGR | 2 | 3015 4548 |
| Mlu113 I ↓ | 2 | 523 4060 |
| CC GC GG<br>GG CG CC ↑ | | |
| MscI ↓ | 1 | 3999 |
| TGG CCA<br>ACC GGT ↑ | | |
| Msl I ↓ | 4 | 1411 3823 3993 4515 |
| CAYNN NNRTG<br>GTANN NNYAC ↑ | | |
| Msp20 I ↓ | 2 | 3996 4002 |
| TGGCCA<br>ACCGGT ↑ | | |
| MspA1 I ↓ | 3 | 524 3778 4061 |
| CMG CKG<br>GKC GMC ↑ | | |
| Noe I ↓ | 1 | 3725 |
| GCC GGC<br>CGG CCG | | |

TABLE 2-continued

| Enzyme | Freq | Position(s) |
|---|---|---|
| Nco I<br>↓<br>C CATG G<br>G GTAC C<br>↑ | 2 | 1406 2707 |
| NgoM I<br>↓<br>G CCGG C<br>C GGCC G<br>↑ | 1 | 3723 |
| Nhe I<br>↓<br>G CTAG C<br>C GATC G<br>↑ | 1 | 3742 |
| Nli387/7 I<br>↓<br>C YCGR G<br>G RGCY C<br>↑ | 5 | 1381 2227 3676 4018 4902 |
| Nru I<br>↓<br>TCG CGA<br>AGC GCT<br>↑ | 1 | 1348 |
| Nsp I<br>↓<br>R CATC Y<br>Y GTAC R<br>↑ | 3 | 54 217 946 |
| Pfl1108 I<br>TCGTAG<br>AGCATC | 2 | 2927 4834 |
| PinAI<br>↓<br>A CCGG T<br>T GGCC A<br>↑ | 1 | 3761 |
| PoeI<br>↓<br>G GGCC C<br>C CCGG G<br>↑ | 2 | 926 2429 |
| Ppu1253 I<br>GACGTC<br>CTGCAG | 1 | 1184 |
| Ppu6-1<br>YACGTR<br>RTGCAY | 4 | 676 1222 2398 2536 |
| Ppu1f I<br>↓<br>RG GWC CY<br>YC CWG GR<br>↑ | 2 | 3017 4550 |
| PshA I<br>↓<br>GACNN NNGTC<br>CTGNN NNCAG<br>↑ | 1 | 4160 |
| Psp1406 I<br>↓<br>AA CG TT<br>TT GC AA<br>↑ | 4 | 1614 1628 3336 4199 |
| PspAI<br>↓<br>C CCGG G<br>G GGCC C<br>↑ | 1 | 1377 |
| Pss I<br>↓<br>RG GNC CY<br>YC CNG GR<br>↑ | 4 | 925 2428 3020 4553 |
| Pvu II<br>↓ | 1 | 3778 |

TABLE 2-continued

| Enzyme | Freq | Position(s) |
|---|---|---|
| CAG CTG<br>GTC GAC<br>↑ | | |
| Rhc I<br>TCATGA<br>AGTACT | 1 | 1472 |
| RieA I<br>↓<br>CCCACANNNNNNNNN NNN<br>GGGTGTNNNNNNNNN NNN<br>↑ | 2 | 3424 5226 |
| Soc I<br>↓<br>G AGCT C<br>C TCGA G<br>↑ | 1 | 1005 |
| Soc II<br>↓<br>CC GC GG<br>GG CG CC<br>↑ | 2 | 525 4062 |
| Sop I<br>↓<br>GCTCTTCN NNN<br>CGAGAAGN NNN<br>↑ | 1 | 993 |
| SouLPI<br>↓<br>GCC GGC<br>CGG CCG<br>↑ | 1 | 3725 |
| Sco I<br>↓<br>AGT ACT<br>TCA TGA<br>↑ | 2 | 654 2475 |
| Sfc I<br>↓<br>C TRYA G<br>G AYRT C<br>↑ | 1 | 4093 |
| SgrA I<br>↓<br>CT CCGG YG<br>GY GGCC RC<br>↑ | 1 | 3723 |
| Sim I<br>↓<br>GGGTC<br>CCCAG<br>↑ | 4 | 2529 2689 4080 5184 |
| Smo I<br>↓<br>CCC GGG<br>GGG CCC<br>↑ | 1 | 1379 |
| SmII<br>↓<br>C TYRA G<br>G ARYT C<br>↑ | 3 | 2854 3662 4922 |
| Sno I<br>GTATAC<br>CATATG | 1 | 1238 |
| SnoB I<br>↓<br>TAC GTA<br>ATG CAT<br>↑ | 1 | 2539 |
| Spe I<br>↓<br>A CTAG T<br>T GATC A<br>↑ | 1 | 3118 |
| Sph I<br>↓<br>G CATG C | 1 | 217 |

TABLE 2-continued

| Enzyme | Freq | Position(s) |
|---|---|---|
| C GTAC G ↑ | | |
| SsoI ↓ | 2 | 671 2173 |
| G AATT C | | |
| C TTAA G ↑ | | |
| Ssp I ↓ | 2 | 362 3408 |
| AAT ATT | | |
| TTA TAA ↑ | | |
| Sst1 ↓ | 1 | 1005 |
| G AGCT C | | |
| C TCGA G ↑ | | |
| Stu I ↓ | 2 | 414 1686 |
| AGG CCT | | |
| TCC GGA ↑ | | |
| StySJ ↓ | 1 | 1411 |
| GAGNNNNNNGTRC | | |
| CTCNNNNNNCAYG ↑ | | |
| StySKI ↓ | 1 | 872 |
| CGATNNNNNNNGTTA | | |
| GCTANNNNNNNCAAT ↑ | | |
| StySP I ↓ | 1 | 2209 |
| AACNNNNNNGTRC | | |
| TTGNNNNNNCAYG ↑ | | |
| Syn II | 3 | 409 1367 3184 |
| GAANNNNTTC | | |
| CTTNNNNAAG | | |
| Toq II ↓ | 3 | 2474 2761 4610 |
| GACCGANNNNNNNNN NN | | |
| CTGGCTNNNNNNNNN NN ↑ | | |
| Toq II ↓ | 1 | 4842 |
| CACCCANNNNNNNNN NN | | |
| CTGGGTNNNNNNNNN NN ↑ | | |
| Tth111 I ↓ | 3 | 326 1131 4242 |
| GACN N NGTC | | |
| CTGN N NCAG ↑ | | |
| Tth111 II ↓ | 3 | 108 2401 4494 |
| CAARCANNNNNNNNN NN | | |
| GYYYGTNNNNNNNNN NN ↑ | | |
| Ubo1220 I | 1 | 1376 |
| CCCGGG | | |
| GGGCCC | | |
| Ubo1303 I | 5 | 870 887 3762 3919 4316 |
| CGRYCG | | |
| GCYRGC | | |
| Ubo1326 I | 4 | 920 2423 3015 4548 |
| RGGNCCY | | |
| YCCNGGR | | |
| Ubo1382 i | 1 | 3265 |
| GAATGC | | |
| CTTACG | | |
| Von91 I ↓ | 1 | 3266 |
| CCAN NNN NTGG | | |
| GGTN NNN NACC ↑ | | |

TABLE 2-continued

| Enzyme | Freq | Position(s) |
|---|---|---|
| Xba I ↓ | 1 | 1679 |
| T CTAG A | | |
| A GATC T ↑ | | |
| Xcm I ↓ | 1 | 1163 |
| CCANNNN N NNNNTGG | | |
| GGTNNNN N NNNNACC ↑ | | |
| Xma I ↓ | 1 | 1377 |
| C CCGG G | | |
| G GGCC C ↑ | | |
| XmoIII ↓ | 2 | 999 3920 |
| C GGCC G | | |
| G CCGG C ↑ | | |
| Xmn I ↓ | 3 | 414 1372 3189 |
| GAANN NNTTC | | |
| CTTNN NNAAG ↑ | | |

What is claimed is:

1. A method for bacterial speciation, said method comprising the steps of:
   i) isolating bacterial DNA from a sample, said sample DNA comprising DNA encoding 16S and 23S rRNA;
   ii) designating one or more bacterial species as control species;
   iii) identifying signature bands for said one or more bacterial control species;
   iv) digesting said isolated sample bacterial DNA with one or more restriction enzymes under conditions such that restriction fragments are produced, said restriction fragments comprising a digestion product of bacterial DNA from said sample, providing one or more restriction enzymes that digest DNA encoding 16S and 23S rRNA from said one or more control species within the region of said DNA encoding 16S rRNA and within the region of said DNA encoding 23S rRNA but not within spacer DNA between said region of said DNA encoding 16S rRNA and said region of said DNA encoding 23S rRNA, said digestion of said one or more control species by said one or more restriction enzymes producing said signature bands for said one or more control species;
   v) separating said restriction fragments;
   vi) detecting said digestion product; and
   vii) comparing the results of said detecting step with said signature bands of said one or more bacterial control species so as to identify bacterial species present in said sample.

2. The method of claim 1, wherein said detecting step comprises reacting a probe with said digestion product under conditions such that said probe hybridizes to one or more restriction fragments in said digestion product.

3. A method for bacterial speciation, comprising;
   a) providing, in any order, i) a first biological sample comprising bacterial DNA from a known bacterial species, and ii) a second biological sample comprising bacterial DNA from a bacterium whose species is unknown;

b) isolating, in any order, i) a first preparation of bacterial DNA from said first sample and ii) a second preparation of bacterial DNA from said second sample, said sample DNA of said first and second preparations comprising DNA encoding 16S and 23S rRNA;

c) digesting, in any order, i) said first preparation of isolated sample DNA with said one or more restriction enzymes under conditions such that a first preparation of restriction fragments is produced, said first preparation of restriction fragments comprising a first digestion product, and ii) said second preparation of isolated sample DNA with said one or more restriction enzymes under conditions such that a second preparation of restriction fragments is produced, said second preparation of restriction fragments comprising a second digestion product, d) separating, in any order, i) said restriction fragments in said first digestion product, ii) said restriction fragments in said second digestion product; and iii) one or more restriction enzymes that digest DNA encoding 16S and 23 S rRNA from said known bacterial species within the region of said DNA encoding 16S rRNA and within the region of said DNA encoding 23S rRNA but not within spacer DNA between said region of said DNA encoding 16 rRNA and said region of said DNA encoding 23S rRNA; and e) comparing said separated first and second digestion products to determine whether said known bacterial species is present in said second biological sample.

4. The method of claim 1, wherein said digesting step comprises using two or more said restriction enzymes, wherein one of said two or more restriction enzymes is known to digest DNA encoding 16S and 23S rRNA within the region of said DNA encoding 16s rRNA but not within spacer DNA between said region of said DNA encoding 16S rRNA and said region of said DNA encoding 23S rRNA, and another of said restriction enzymes is known to digest DNA encoding 16S and 23S rRNA within the region of said DNA encoding 23S rRNA but not within spacer DNA between said region of said DNA encoding 16S rRNA and said region of said DNA encoding 23S rRNA.

5. The method of claim 1, wherein in said digesting step, one of said one or more restriction enzymes is known to digest DNA encoding 16S and 23S rRNA both within the region of said DNA encoding 16S rRNA and within the region of said DNA encoding 23S rRNA but not within spacer DNA between said region of said DNA enoding 16S rRNA and said region of said DNA encoding 23S rRNA.

6. A method for identifying species-specific signature bands for bacterial speciation, comprising:

i) identifying an a priori signature band for a known bacterial species, wherein said identifying step comprises inspecting the nucleic acid sequence of a 16S rRNA gene and a 23S rRNA gene in a ribosomal operon of an isolate of said known bacterial species, determining by said inspection a restriction enzyme that digests DNA encoding 16S and 23S rRNA within the region of said DNA encoding 16S rRNA and within the region of said DNA encoding 23S rRNA but not within spacer DNA between said region of said DNA encoding 16S rRNA and said region of said DNA encoding 23S rRNA, and denominating the fragment of DNA between said digestion sites as an a priori signature band;

ii) providing a plurality of biological samples, each said sample comprising bacterial DNA from a different isolate of said known bacterial species;

iii) isolating a preparation of bacterial DNA from each of said samples, said sample DNA of each of said preparations comprising DNA encoding 16S and 23S rRNA;

iv) digesting each said preparation of isolated sample DNA with said restriction enzyme under conditions such that restriction fragments are produced, said restriction fragments for each of said preparations comprising a digestion product of bacterial DNA from said isolate, v) separating said restriction fragments in said digestion products for each of said preparations;

vi) detecting each said digestion product; and vii) comparing the results of said detecting steps for all of said preparations to determine conserved species-specific signature bands for said known bacterial species.

7. A method for identifying species-specific signature bands for bacterial speciation, comprising:

i) providing a plurality of biological samples, each said sample comprising bacterial DNA from a different isolate of said known bacterial species;

ii) isolating a preparation of bacterial DNA from each of said samples, said sample DNA of each of said preparations comprising DNA encoding 16S and 23S rRNA;

iii) providing one or more restriction enzymes that digest DNA encoding 16S and 23S r RNA from said known bacterial species within the region of said DNA encoding 16S rRNA and within the region of said DNA encoding 23S rRNA but not within spacer DNA between said region of said DNA encoding 16S rRNA and said region of said DNA encoding 23S rRNA, said digestion of said known bacterial species by said one or more restriction enzymes producing said signature bands for said known bacterial species;

iv) digesting each said preparation of isolated sample DNA with said one or more restriction enzymes under conditions such that restriction fragments are produced, said restriction fragments for each of said preparations comprising a digestion product of bacterial DNA from said isolate, iv) separating said restriction fragments in said digestion products for each of said preparations;

v) detecting each said digestion product; and vi) comparing the results of said detecting steps for all of said preparations to determine conserved bands for said known bacterial species, said conserved bands being denominated species-specific signature bands.

* * * * *

UNITED STATES PATENT AND TRADEMARK OFFICE
CERTIFICATE OF CORRECTION

PATENT NO. : 6,630,302 B1  Page 1 of 2
APPLICATION NO. : 09/463588
DATED : October 7, 2003
INVENTOR(S) : Richard N. Goldstein It is certified that error appears in the above-identified patent and that said Letters Patent is hereby corrected as shown below:

Column 8, line 48, "oligpnucleotide" should read --oligonucleotide--;

Column 11, line 46, "Chiamydia" should read --Chlamydia--;

Column 15, line 38, "electrophoesis" should read --electrophoresis--;

Column 16, line 64, "catabolizedby" should read --catabolized by--;

Column 18, line 60, "analysed" should read --analyzed--;

Column 56, claim 1, starting at line 28, delete claim 1 and insert the following claim 1:

--1.  A method for bacterial speciation, said method comprising the steps of:
  i)  isolating bacterial DNA from a sample, said sample DNA comprising DNA encoding 16S and 23S rRNA;

ii)  designating one or more bacterial species as control species;

iii)  identifying signature bands for said one or more bacterial control species;

iv)  providing one or more restriction enzymes that digest DNA encoding 16S and 23S rRNA from said one or more control species within the region of said DNA encoding 16S rRNA and within the region of said DNA encoding 23S rRNA but not within spacer DNA between said region of said DNA encoding 16S rRNA and said region of said DNA encoding 23S rRNA, said digestion of said one or more control species by said one or more restriction enzymes producing said signature bands for said one or more control species;

v)  digesting said isolated sample bacterial DNA with said one or more restriction enzymes under conditions such that restriction fragments are produced, said restriction fragments comprising a digestion product of bacterial DNA from said sample;

vi)  separating said restriction fragments;

UNITED STATES PATENT AND TRADEMARK OFFICE
CERTIFICATE OF CORRECTION

| | | |
|---|---|---|
| PATENT NO. | : 6,630,302 B1 | |
| APPLICATION NO. | : 09/463588 | |
| DATED | : October 7, 2003 | |
| INVENTOR(S) | : Richard N. Goldstein | |

It is certified that error appears in the above-identified patent and that said Letters Patent is hereby corrected as shown below:

vii)     detecting said digestion product; and viii)    comparing the results of said detecting step with said signature bands of said one or more bacterial control species so as to identify bacterial species present in said sample.--

Column 56, claim 3, line 66, "unknown;" should read as follows:

--unknown, and iii) one or more restriction enzymes that digest DNA encoding 16S and 23S rRNA from said known bacterial species within the region of said DNA encoding 16S rRNA and within the region of said DNA encoding 23S rRNA but not within spacer DNA between said region of said DNA encoding 16S rRNA and said region of said DNA encoding 23S rRNA;-- and

Column 57, claim 6, line 56, "enzyme that digests" should read --enzyme capable of digesting--.

Signed and Sealed this

First Day of July, 2008

JON W. DUDAS
*Director of the United States Patent and Trademark Office*